(12) United States Patent
Davies et al.

(10) Patent No.: US 11,224,349 B2
(45) Date of Patent: Jan. 18, 2022

(54) DEVICES, SYSTEMS, AND METHODS FOR ASSESSING A VESSEL WITH AUTOMATED DRIFT CORRECTION

(71) Applicants: VOLCANO CORPORATION, San Diego, CA (US); IMPERIAL INNOVATIONS LIMITED, London (GB)

(72) Inventors: Justin Davies, London (GB); Joseph Burnett, Carlsbad, CA (US)

(73) Assignees: IMAGE GUIDE THERAPY CORPORATION, San Diego, CA (US); IMPERIAL INNOVATIONS LIMITED, London (GB)

(*) Notice: Subject to any disclaimer, the term of this patent is extended or adjusted under 35 U.S.C. 154(b) by 1121 days.

(21) Appl. No.: 14/335,680

(22) Filed: Jul. 18, 2014

(65) Prior Publication Data
US 2015/0025398 A1    Jan. 22, 2015

Related U.S. Application Data

(60) Provisional application No. 61/856,518, filed on Jul. 19, 2013.

(51) Int. Cl.
*A61B 5/0215* (2006.01)
*A61B 5/02* (2006.01)
(Continued)

(52) U.S. Cl.
CPC ........ *A61B 5/0215* (2013.01); *A61B 5/02007* (2013.01); *A61B 5/02158* (2013.01);
(Continued)

(58) Field of Classification Search
None
See application file for complete search history.

(56) References Cited

U.S. PATENT DOCUMENTS 5,422,478 A * 6/1995 Wlodarczyk ...... A61B 5/02154
250/227.21
5,964,714 A * 10/1999 Lafontaine ........... A61B 5/0215
600/561
(Continued)

FOREIGN PATENT DOCUMENTS

| EP | 2345365 A1 | 7/2011 |
|---|---|---|
| JP | 11128180 A | 5/1999 |
| WO | 2013028612 A2 | 2/2013 |

OTHER PUBLICATIONS

Pascal Vranckx, Coronary Pressure-Derived Fractional Flow REserve Measurements, Apr. 17, 2012, Circulation: Cardiovascular Interventions, vol. 5, Issue 2, pp. 312-316.*
(Continued)

*Primary Examiner* — Sean P Dougherty
*Assistant Examiner* — Alexander H Connor

(57) ABSTRACT

Embodiments of the present disclosure are configured to assess the severity of a blockage in a vessel and, in particular, a stenosis in a blood vessel. In some particular embodiments, the devices, systems, and methods of the present disclosure are configured to assess the severity of a stenosis in the coronary arteries without the administration of a hyperemic agent. In some embodiments, the devices, systems, and methods of the present disclosure are configured to assess a vessel by automatically correcting for drift in the equipment utilized to obtain measurements related to the vessel.

19 Claims, 18 Drawing Sheets

(51) Int. Cl.
*A61B 5/107* (2006.01)
*A61B 5/00* (2006.01)

(52) U.S. Cl.
CPC ........... *A61B 5/1076* (2013.01); *A61B 5/7225* (2013.01); *A61B 5/7239* (2013.01); *A61B 2560/0223* (2013.01)

(56) References Cited

U.S. PATENT DOCUMENTS

| | | | |
|---|---|---|---|
| 6,565,514 B2* | 5/2003 | Svanerudh | A61B 5/6851 |
| | | | 600/485 |
| 8,182,429 B2 | 5/2012 | Martin | |
| 2002/0072647 A1 | 6/2002 | Schock | |
| 2003/0032886 A1 | 2/2003 | Elhanan | |
| 2004/0019285 A1* | 1/2004 | Eigler | A61B 5/0215 |
| | | | 600/488 |
| 2011/0100136 A1* | 5/2011 | Chouzenoux | G01F 1/44 |
| | | | 73/861.63 |
| 2012/0053921 A1* | 3/2012 | Taylor | A61B 5/4848 |
| | | | 703/11 |
| 2013/0131523 A1* | 5/2013 | Suchecki | A61B 5/02007 |
| | | | 600/486 |
| 2013/0345574 A1* | 12/2013 | Davies | A61B 5/02007 |
| | | | 600/486 |

OTHER PUBLICATIONS

Tim Shorter, All Sensors, Mar. 4, 2012, pp. 1-4.*
Joel Reiter, Drift Measurements in Pressure Sensors, Feb. 2012, Sea-Bird Electronics, pp. 1-3 (Year: 2012).*

* cited by examiner

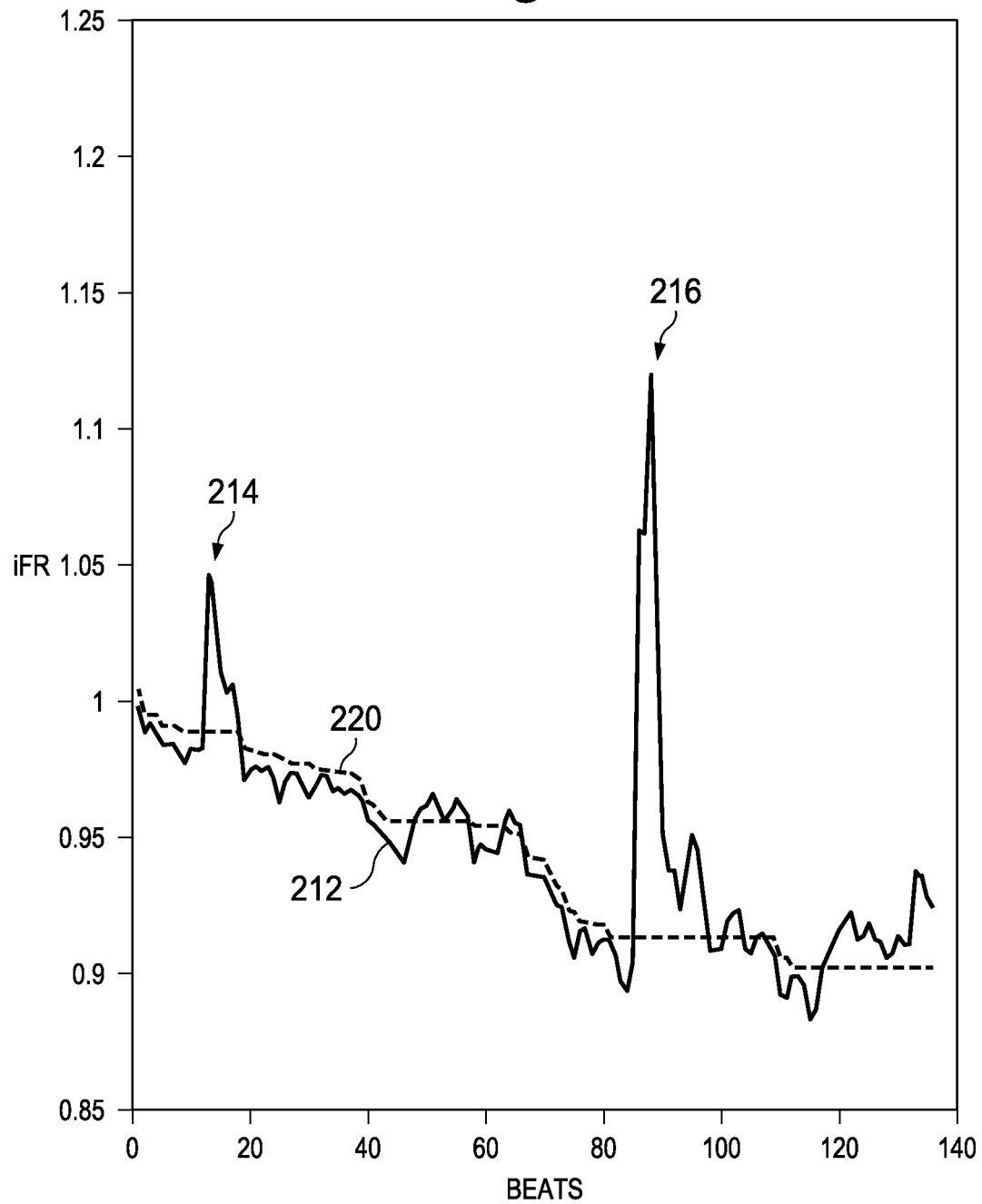

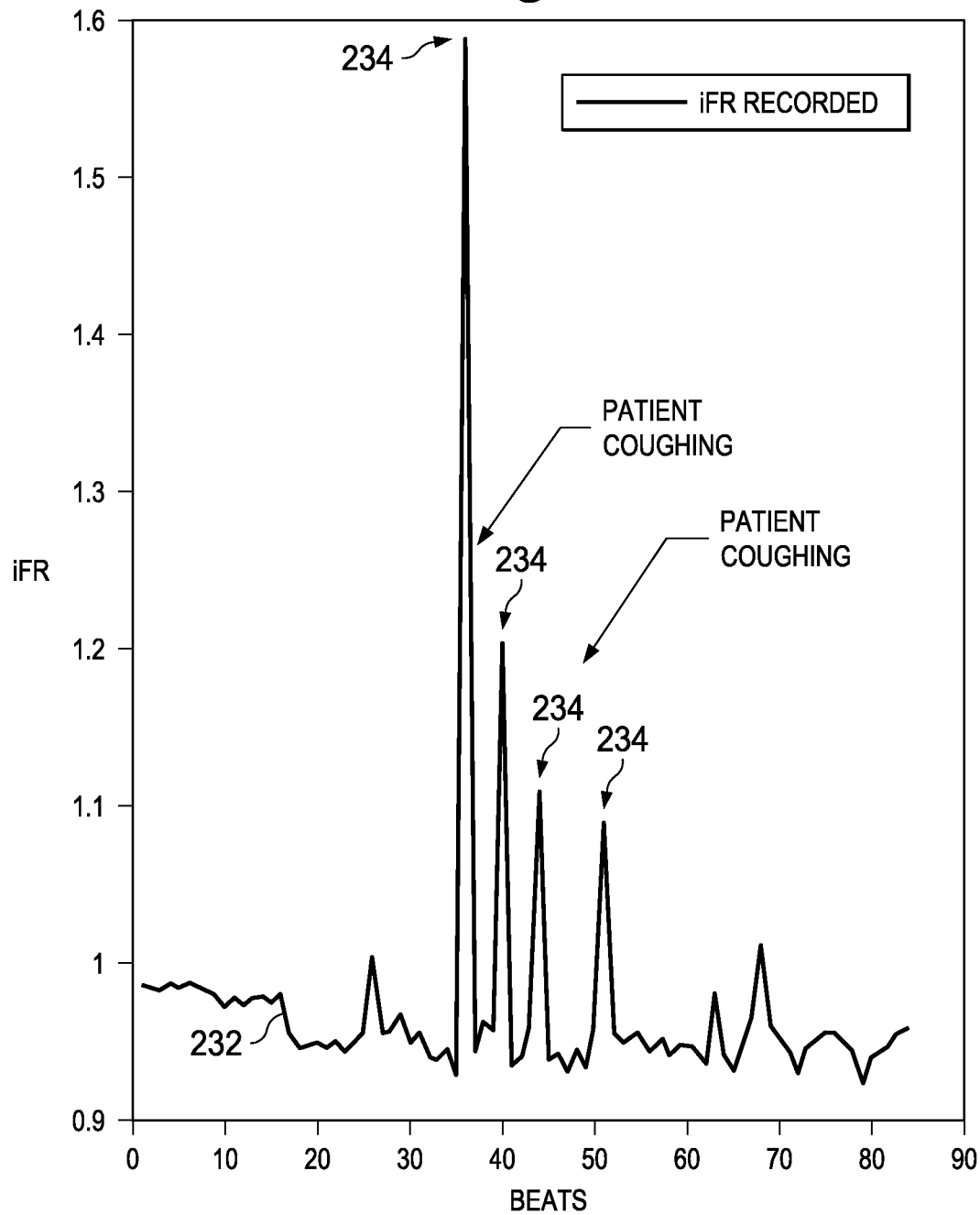

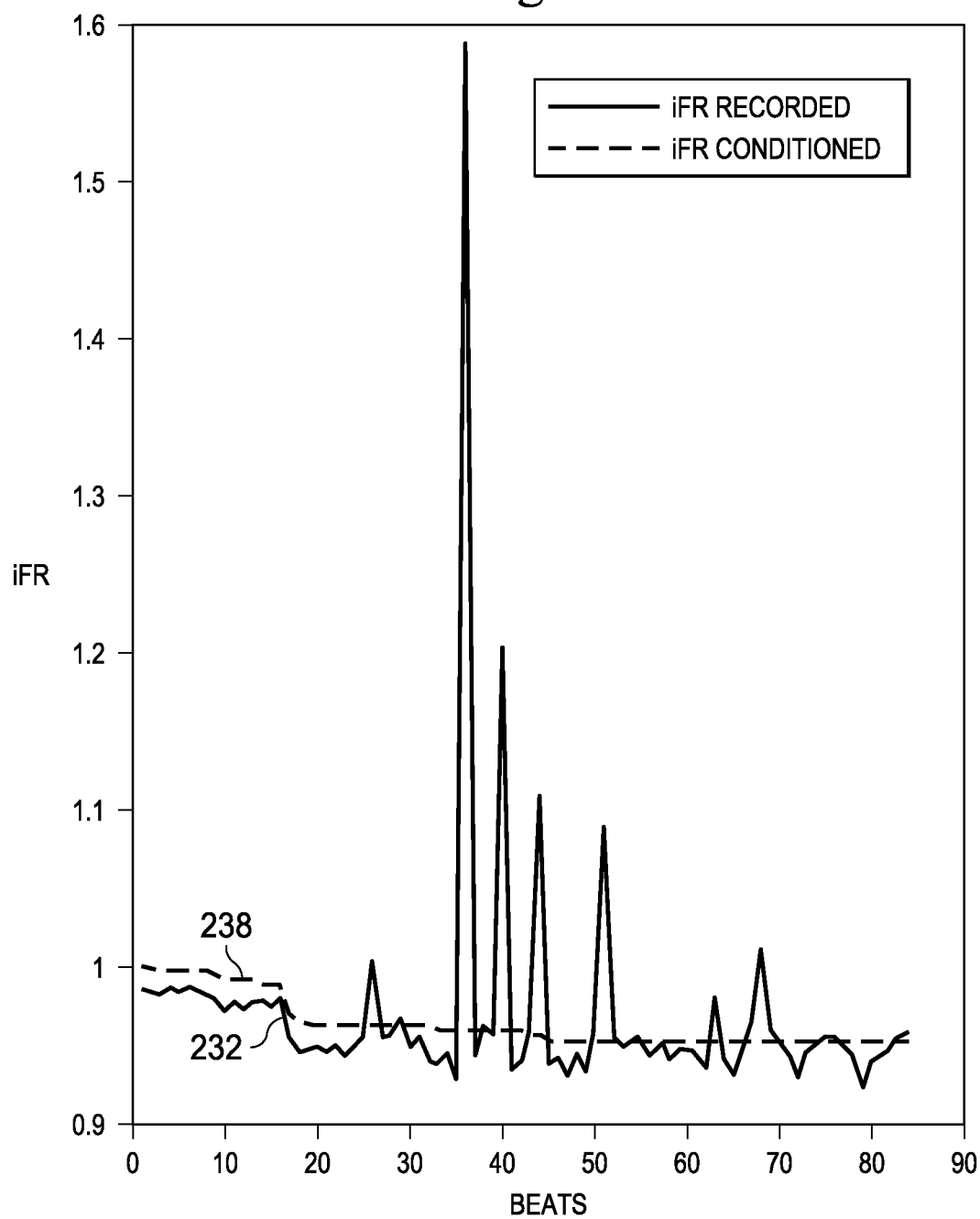

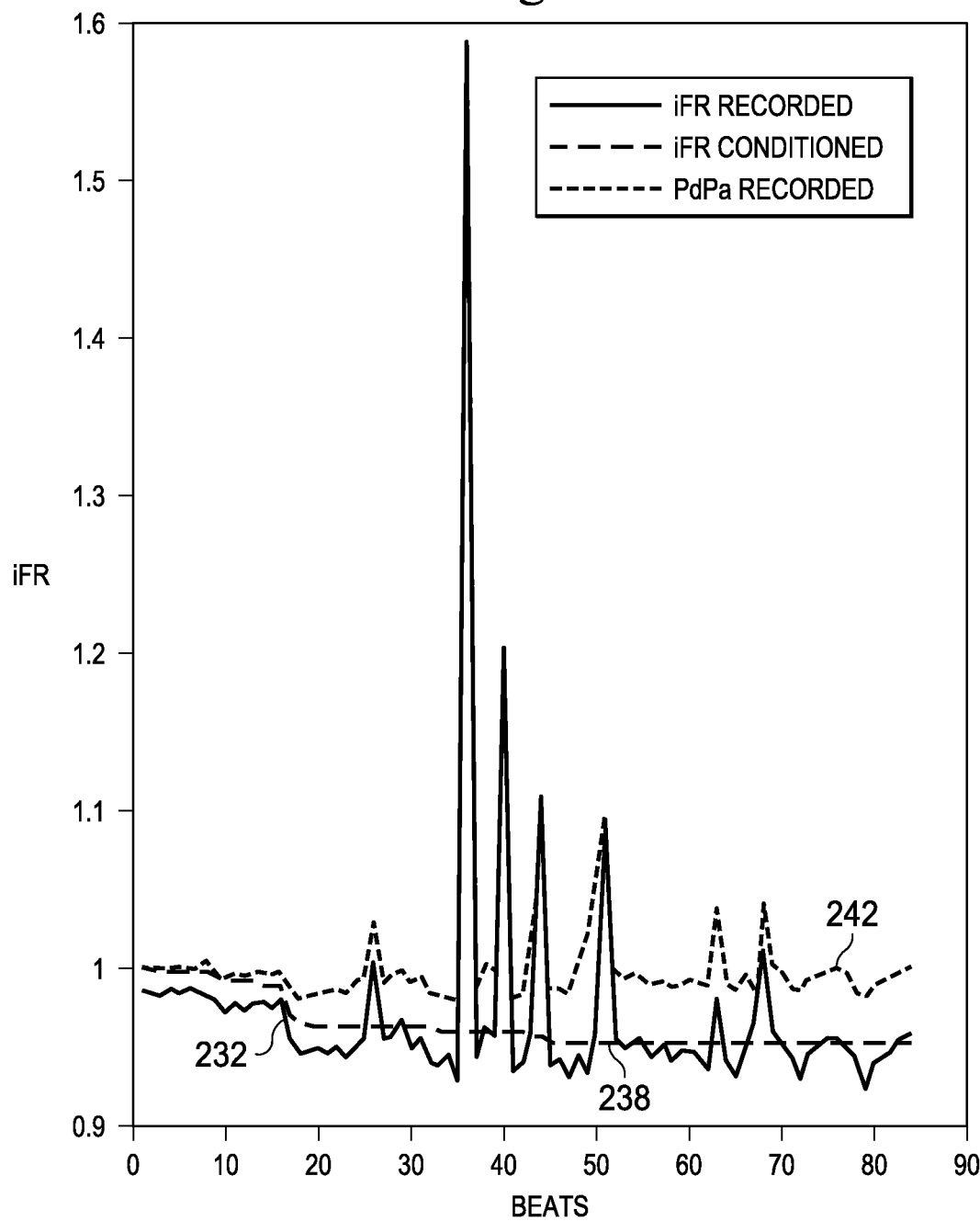

DEVICES, SYSTEMS, AND METHODS FOR ASSESSING A VESSEL WITH AUTOMATED DRIFT CORRECTION

CROSS-REFERENCE TO RELATED APPLICATION

The present application claims the benefit of the filing date of provisional U.S. Patent Application No. 61/856,518 filed Jul. 19, 2013. The entire disclosure of this provisional application is incorporated herein by this reference.

TECHNICAL FIELD

The present disclosure relates generally to the assessment of vessels and, in particular, the assessment of the severity of a blockage or other restriction to the flow of fluid through a vessel. Aspects of the present disclosure are particularly suited for evaluation of biological vessels in some instances. For example, some particular embodiments of the present disclosure are specifically configured for the evaluation of a stenosis of a human blood vessel.

BACKGROUND

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include angioplasty and stenting.

Coronary blood flow is unique in that it is affected not only by fluctuations in the pressure arising proximally (as in the aorta) but is also simultaneously affected by fluctuations arising distally in the microcirculation. Accordingly, it is not possible to accurately assess the severity of a coronary stenosis by simply measuring the fall in mean or peak pressure across the stenosis because the distal coronary pressure is not purely a residual of the pressure transmitted from the aortic end of the vessel. As a result, for an effective calculation of FFR within the coronary arteries, it is necessary to reduce the vascular resistance within the vessel. Currently, pharmacological hyperemic agents, such as adenosine, are administered to reduce and stabilize the resistance within the coronary arteries. These potent vasodilator agents reduce the dramatic fluctuation in resistance (predominantly by reducing the microcirculation resistance associated with the systolic portion of the heart cycle) to obtain a relatively stable and minimal resistance value.

However, the administration of hyperemic agents is not always possible or advisable. First, the clinical effort of administering hyperemic agents can be significant. In some countries (particularly the United States), hyperemic agents such as adenosine are expensive, and time consuming to obtain when delivered intravenously (IV). In that regard, IV-delivered adenosine is generally mixed on a case-by-case basis in the hospital pharmacy. It can take a significant amount of time and effort to get the adenosine prepared and delivered to the operating area. These logistic hurdles can impact a physician's decision to use FFR. Second, some patients have contraindications to the use of hyperemic agents such as asthma, severe COPD, hypotension, bradycardia, low cardiac ejection fraction, recent myocardial infarction, and/or other factors that prevent the administration of hyperemic agents. Third, many patients find the administration of hyperemic agents to be uncomfortable, which is only compounded by the fact that the hyperemic agent may need to be applied multiple times during the course of a procedure to obtain FFR measurements. Fourth, the administration of a hyperemic agent may also require central venous access (e.g., a central venous sheath) that might otherwise be avoided. Finally, not all patients respond as expected to hyperemic agents and, in some instances, it is difficult to identify these patients before administration of the hyperemic agent.

Accordingly, there remains a need for improved devices, systems, and methods for assessing the severity of a blockage in a vessel and, in particular, a stenosis in a blood vessel. In that regard, there remains a need for improved devices, systems, and methods for assessing the severity of a stenosis in the coronary arteries that do not require the administration of hyperemic agents.

SUMMARY

Embodiments of the present disclosure are configured to assess the severity of a blockage in a vessel and, in particular, a stenosis in a blood vessel without the administration of a hyperemic agent that automatically correct for drift in the instrument(s) utilized to obtain data related to the vessel.

In some instances, a method of evaluating a vessel of a patient is provided. The method includes normalizing pressure measurements of a first pressure sensing device and a second pressure sensing device to one another; obtaining first pressure measurements from the first pressure sensing device within the vessel at a position proximal of a stenosis of the vessel; obtaining second pressure measurements from the second pressure sensing device within the vessel as the second pressure sensing device is moved from a position distal of the stenosis to a position proximal of the stenosis; determining an offset between the first pressure measurements and the second pressure measurements obtained with the second pressure sensing device positioned proximal of the stenosis after the second pressure sensing device is moved from the position distal of the stenosis to the position proximal of the stenosis; calculating a pressure ratio between the second pressure measurements and the first pressure measurements that automatically corrects for the offset between the first pressure measurements and the second pressure measurements obtained with the second pressure sensing device positioned proximal of the stenosis; and outputting the calculated pressure ratio to a display.

In some implementations, the calculated pressure ratio automatically corrects for the offset by adding a fixed value to the pressure ratio between the second pressure measurements and the first pressure measurements. The fixed value may increase or decrease the pressure ratio. In other implementations, the calculated pressure ratio automatically corrects for the offset by adding a variable value, either linear or non-linear, to the pressure ratio between the second pressure measurements and the first pressure measurements. In some instances, the calculated pressure ratio is constrained such that the pressure ratios increase in correspondence with the second pressure sensing device moving from the position distal of the stenosis to the position proximal of the stenosis. In some embodiments, the first pressure sensing device is a catheter and the second pressure sensing device is a guidewire.

In another embodiment, a method of evaluating a vessel of a patient is provided that includes normalizing a first pressure sensing device to a second pressure sensing device; after normalizing, obtaining pressure measurements from within a vessel with the first and second pressure sensing devices; after obtaining the pressure measurements from within the vessel, positioning the first and second pressure sensing devices adjacent to one another in the vessel and determining an offset between the pressure measurements of the first and second pressure sensing devices when positioned adjacent to one another; calculating a pressure ratio between the pressure measurements obtained within the vessel by the first and second pressure sensing devices that automatically corrects for the offset; and outputting the calculated pressure ratio to a display.

Systems specifically configured to implement such methods are also provided.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 15 is a graphical representation of pressure measurements obtained from within a vessel similar to FIG. 14, but showing a modified plot removing the effects of the disruptions in the pressure measurements according to an embodiment of the present disclosure.

FIG. 16 is a graphical representation of pressure measurements obtained from within a vessel having physiological disruptions in the pressure measurements according to an embodiment of the present disclosure.

FIG. 17 is a graphical representation of pressure measurements obtained from within a vessel similar to FIG. 16, but showing a modified plot removing the effects of the physiological disruptions in the pressure measurements according to an embodiment of the present disclosure.

FIG. 18 is a graphical representation of pressure measurements obtained from within a vessel similar to FIGS. 16 and 17, but showing a plot of the pressure measurements according to an embodiment of the present disclosure.

DETAILED DESCRIPTION

Figure 1:
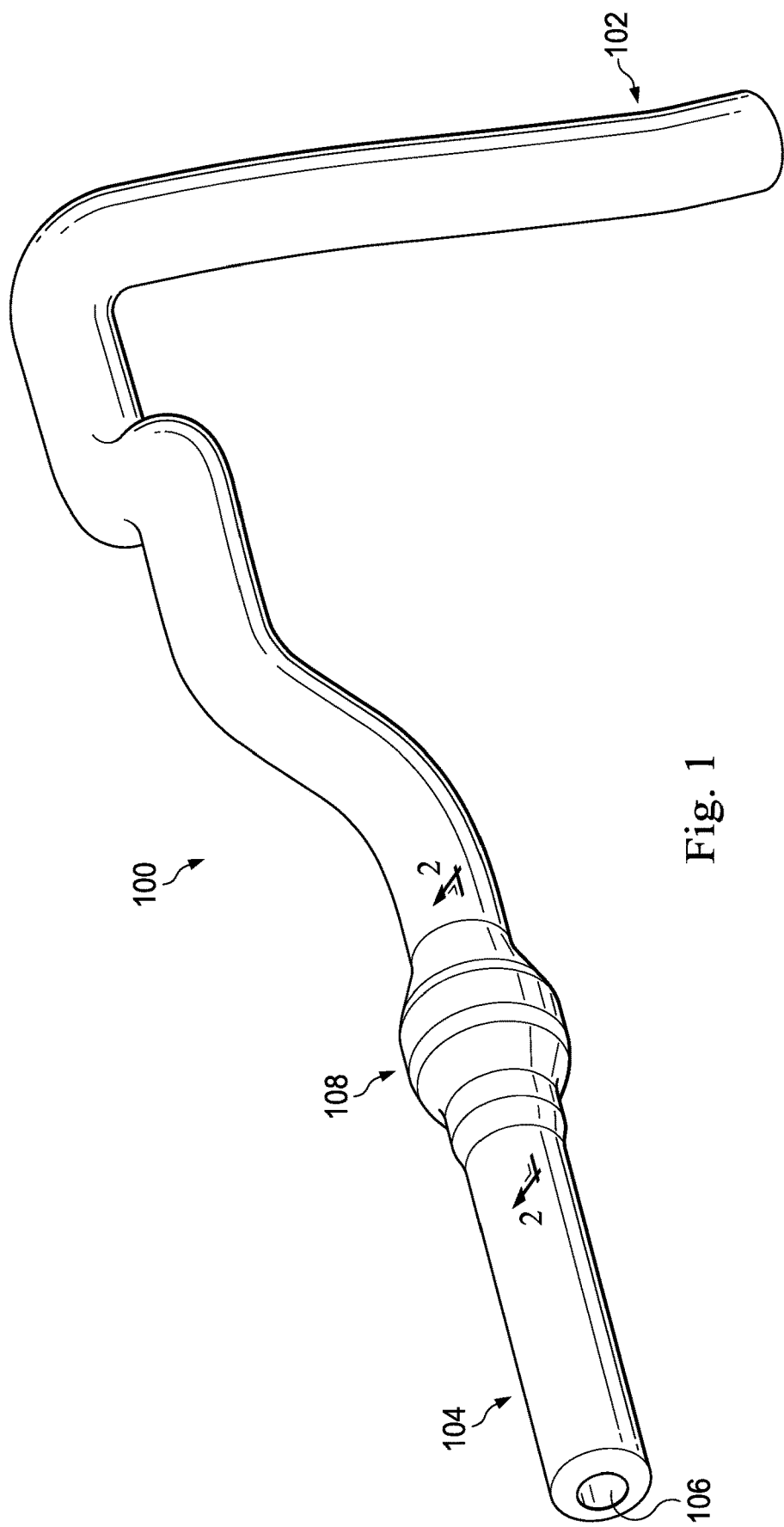
FIG. 1 is a diagrammatic perspective view of a vessel having a stenosis according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 2:
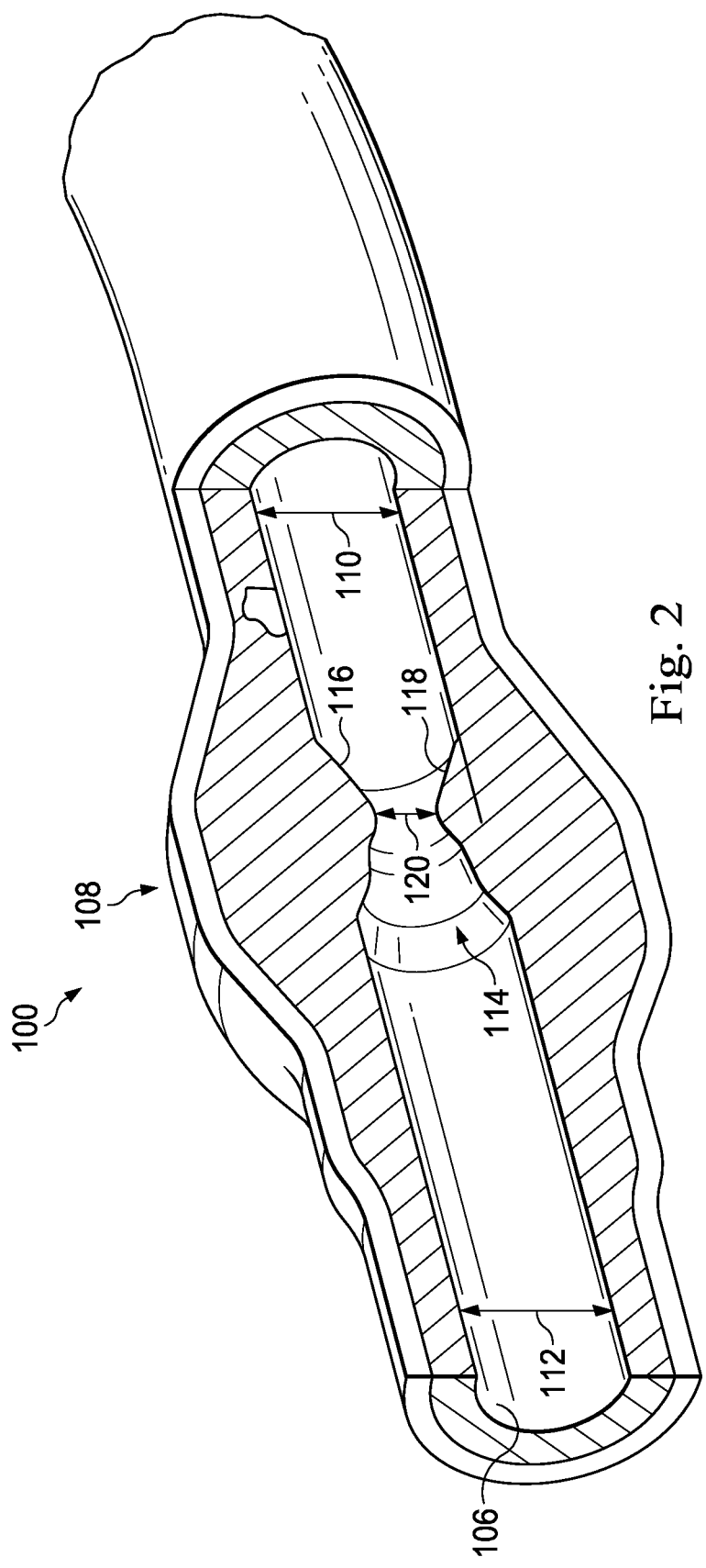
FIG. 2 is a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a systemic blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
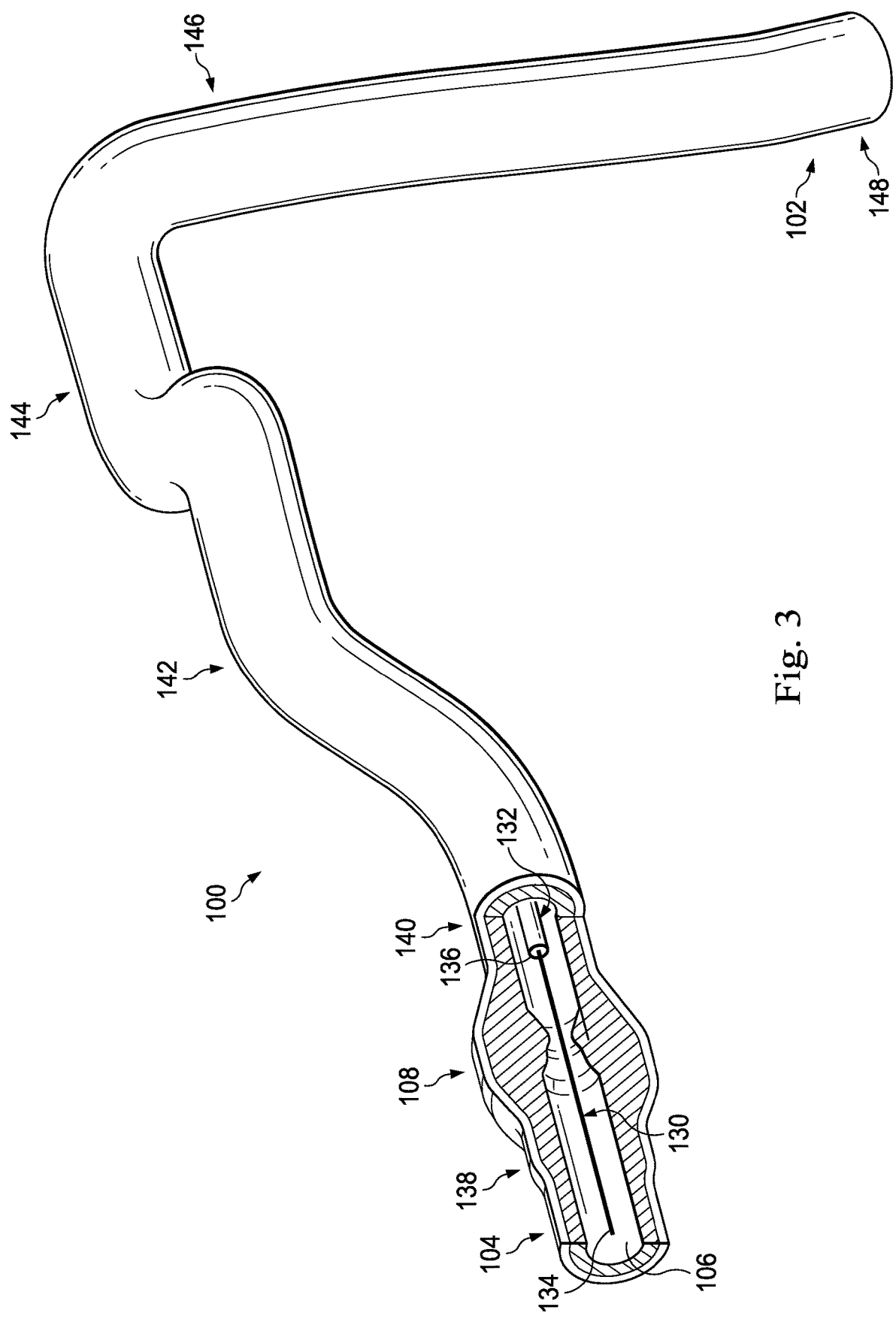
FIG. 3 is a diagrammatic, partial cross-sectional perspective view of the vessel of FIGS. 1 and 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may be any form of device, instrument, or probe sized and shaped to be positioned within a vessel. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In that regard, the single instrument incorporates aspects of the functionalities (e.g., data acquisition) of both instruments 130 and 132 in some embodiments.

Instrument 130 is configured to obtain diagnostic information about the vessel 100. In that regard, the instrument 130 includes one or more sensors, transducers, and/or other monitoring elements configured to obtain the diagnostic information about the vessel. The diagnostic information includes one or more of pressure, flow (velocity), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the PrimeWire PRESTIGE® pressure guide wire, the PrimeWire® pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 130 is sized such that it can be positioned through the stenosis 108 without significantly impacting fluid flow across the stenosis, which would impact the distal pressure reading. Accordingly, in some instances the instrument 130 has an outer diameter of 0.018" or less. In some embodiments, the instrument 130 has an outer diameter of 0.014" or less.

Instrument 132 is also configured to obtain diagnostic information about the vessel 100. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The diagnostic information obtained by instrument 132 includes one or more of pressure, flow (velocity), images (including images obtained using ultrasound (e.g., IVUS), OCT, thermal, and/or other imaging techniques), temperature, and/or combinations thereof. Instrument 132 includes one or more sensors, transducers, and/or other monitoring elements configured to obtain this diagnostic information. In that regard, the one or more sensors, transducers, and/or other monitoring elements are positioned adjacent a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

Similar to instrument 130, instrument 132 also includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Millar catheters are utilized in some embodiments. Currently available catheter products suitable for use with one or more of Philips's Xper Flex Cardio Physiomonitoring System, GE's Mac-Lab XT and XTi hemodynamic recording systems, Siemens's AXIOM Sensis XP VC11, McKesson's Horizon Cardiology Hemo, and Mennen's Horizon XVu Hemodynamic Monitoring System and include pressure monitoring elements can be utilized for instrument 132 in some instances.

In accordance with aspects of the present disclosure, at least one of the instruments 130 and 132 is configured to monitor a pressure within the vessel 100 distal of the stenosis 108 and at least one of the instruments 130 and 132 is configured to monitor a pressure within the vessel proximal of the stenosis. In that regard, the instruments 130, 132 are sized and shaped to allow positioning of the at least one element configured to monitor pressure within the vessel 100 to be positioned proximal and/or distal of the stenosis 108 as necessary based on the configuration of the devices. In that regard, FIG. 3 illustrates a position 138 suitable for measuring pressure distal of the stenosis 108. In that regard, the position 138 is less than 5 cm, less than 3 cm, less than 2 cm, less than 1 cm, less than 5 mm, and/or less than 2.5 mm from the distal end of the stenosis 108 (as shown in FIG. 2) in some instances. FIG. 3 also illustrates a plurality of suitable positions for measuring pressure proximal of the stenosis 108. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

In some embodiments, at least one of the instruments 130 and 132 is configured to monitor pressure within the vessel 100 while being moved through the lumen 106. In some instances, instrument 130 is configured to be moved through the lumen 106 and across the stenosis 108. In that regard, the instrument 130 is positioned distal of the stenosis 108 and moved proximally (i.e., pulled back) across the stenosis to a position proximal of the stenosis in some instances. In other instances, the instrument 130 is positioned proximal of the stenosis 108 and moved distally across the stenosis to a position distal of the stenosis. Movement of the instrument 130, either proximally or distally, is controlled manually by medical personnel (e.g., hand of a surgeon) in some embodiments. In other embodiments, movement of the instrument 130, either proximally or distally, is controlled automatically by a movement control device (e.g., a pullback device, such as the Trak Back® II Device available from Volcano Corporation). In that regard, the movement control device controls the movement of the instrument 130 at a selectable and known speed (e.g., 2.0 mm/s, 1.0 mm/s, 0.5 mm/s, 0.2 mm/s, etc.) in some instances. Movement of the instrument 130 through the vessel is continuous for each pullback or push through, in some instances. In other instances, the instrument 130 is moved step-wise through the vessel (i.e., repeatedly moved a fixed amount of distance and/or a fixed amount of time). Some aspects of the visual depictions discussed below are particularly suited for embodiments where at least one of the instruments 130 and 132 is moved through the lumen 106. Further, in some particular instances, aspects of the visual depictions discussed below are particularly suited for embodiments where a single instrument is moved through the lumen 106, with or without the presence of a second instrument.

Figure 4:
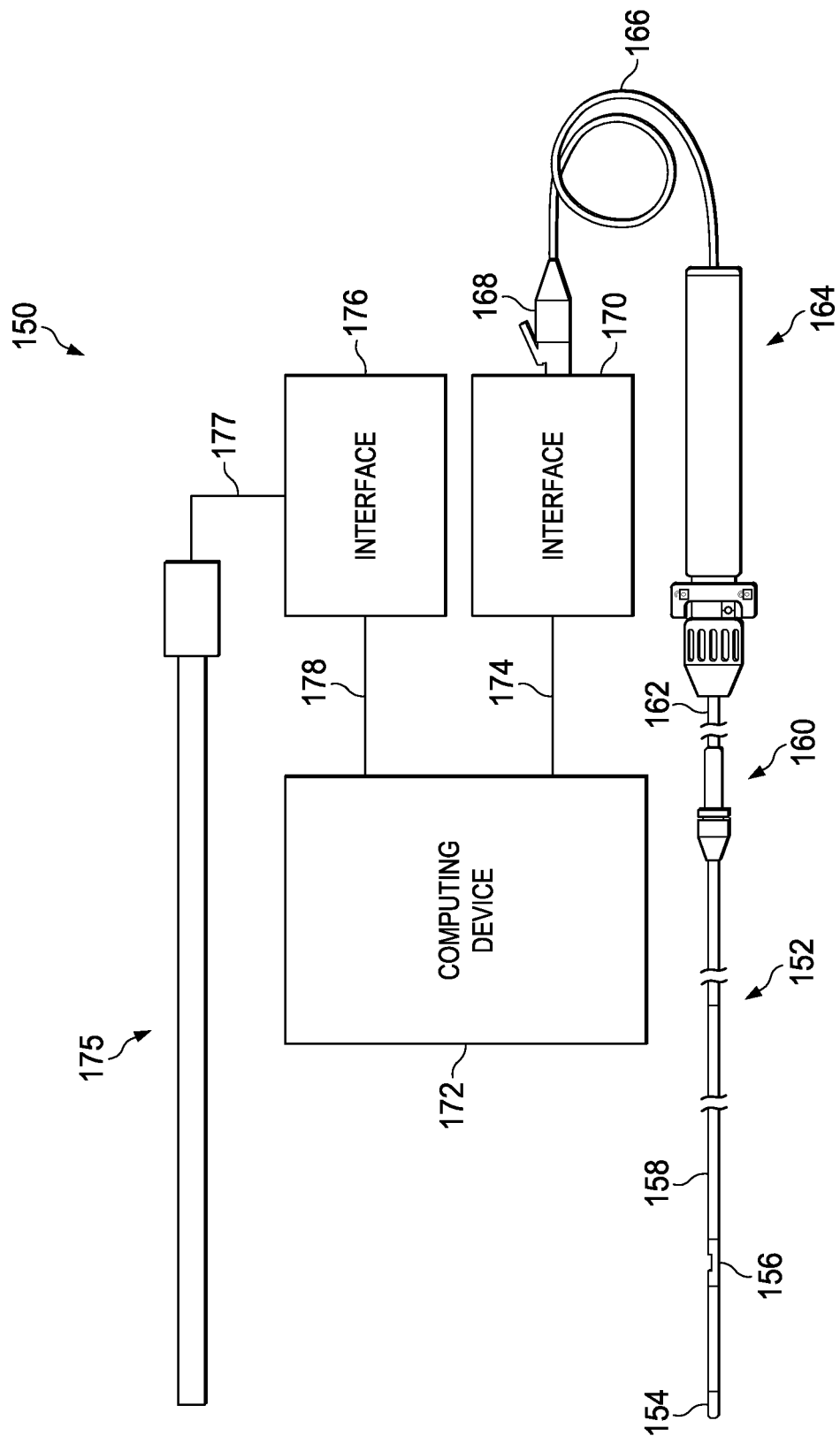
FIG. 4 is a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances instrument 152 is suitable for use as at least one of instruments 130 and 132 discussed above. Accordingly, in some instances the instrument 152 includes features similar to those discussed above with respect to instruments 130 and 132 in some instances. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 172 is a console device. In some particular instances, the computing device 172 is similar to the s5™ Imaging System or the s5i™ Imaging System, each available from Volcano Corporation. In some instances, the computing device 172 is portable (e.g., handheld, on a rolling cart, etc.). Further, it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes an instrument 175. In that regard, in some instances instrument 175 is suitable for use as at least one of instruments 130 and 132 discussed above. Accordingly, in some instances the instrument 175 includes features similar to those discussed above with respect to instruments 130 and 132 in some instances. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis, Mennen Horizon XVu, and Philips Xper IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof. In that regard, it is understood that the connection 178 is wireless in some instances. In some instances, the connection 178 includes a communication link over a network (e.g., intranet, internet, telecommunications network, and/or other network). In that regard, it is understood that the computing device 172 is positioned remote from an operating area where the instrument 175 is being used in some instances. Having the connection 178 include a connection over a network can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

Figure 5:
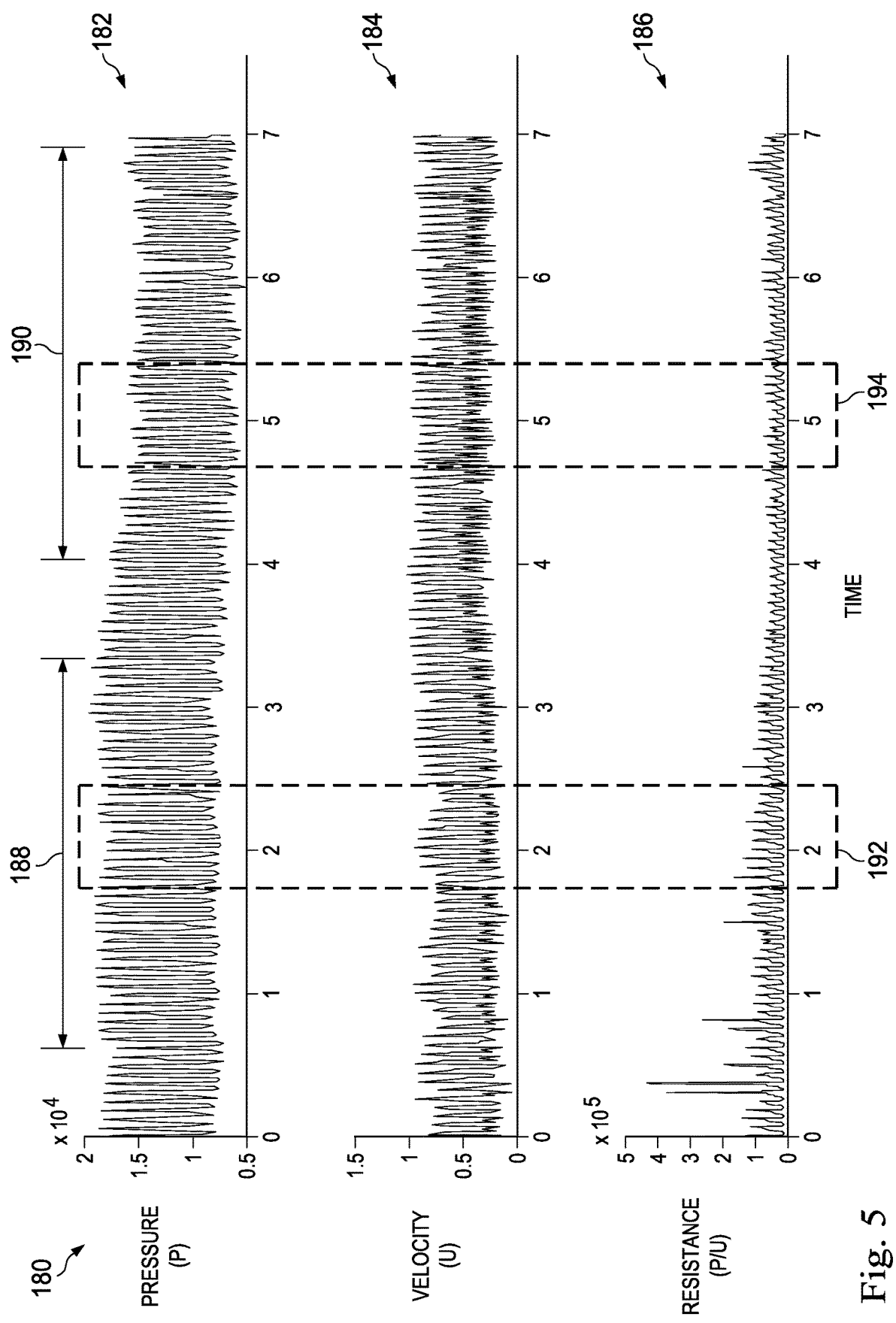
FIG. 5 is a graphical representation of measured pressure, velocity, and resistance within a vessel according to an embodiment of the present disclosure.
Figure 6:
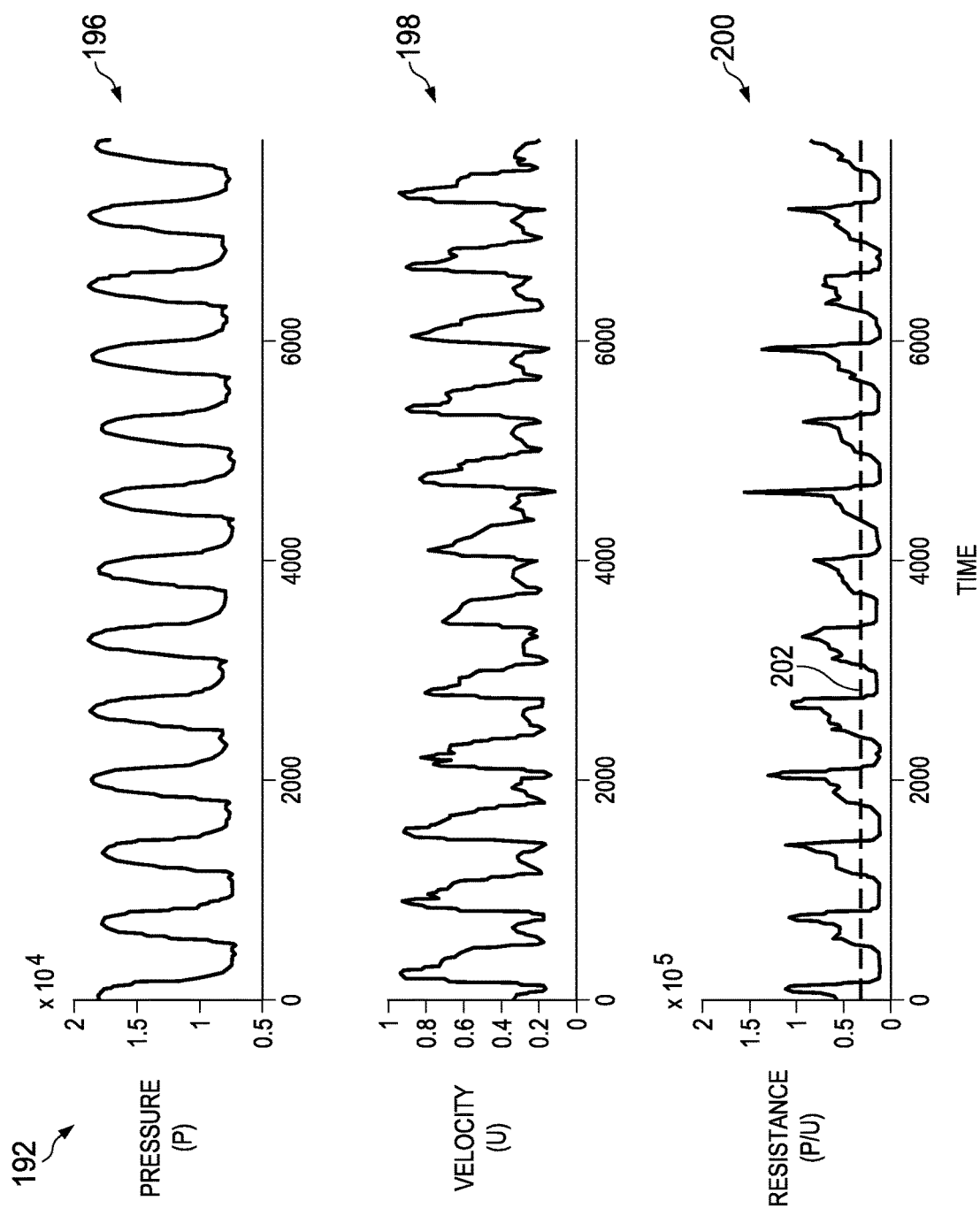
FIG. 6 is a magnified view of a portion of the graphical representation of FIG. 5 corresponding to a resting state of a patient.
Figure 7:
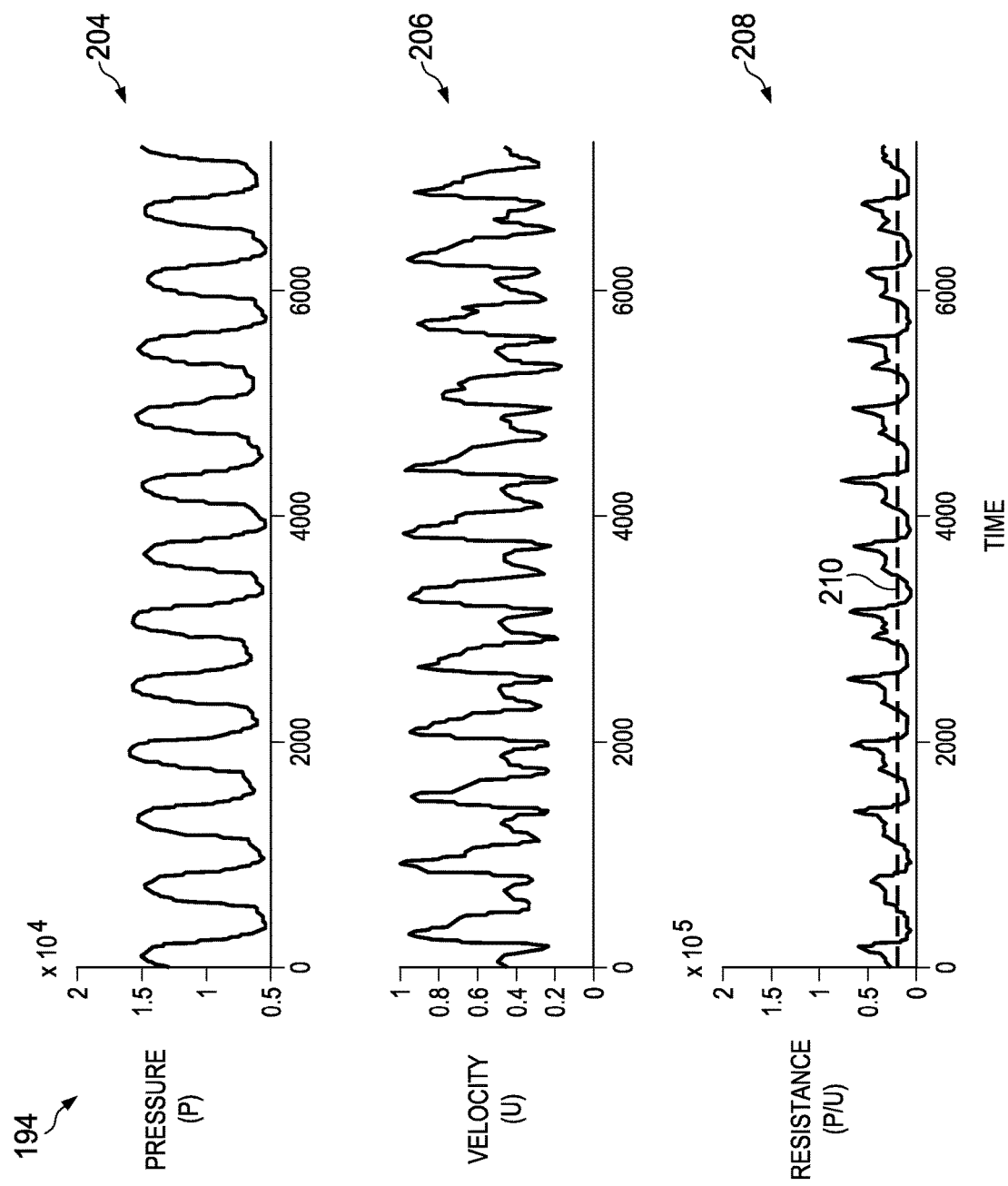
FIG. 7 is a magnified view of a portion of the graphical representation of FIG. 5 corresponding to a hyperemic state of a patient.
Figure 8:
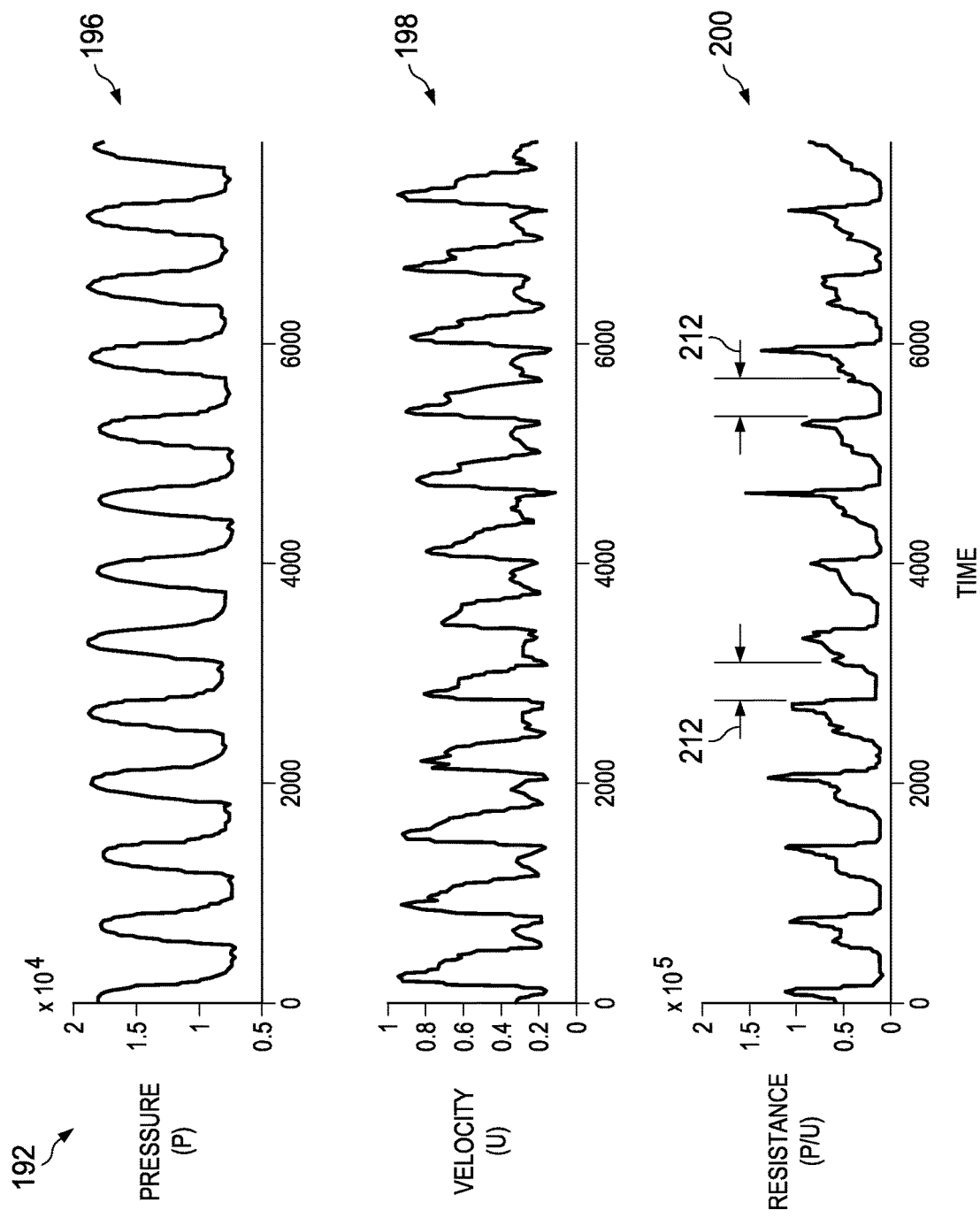
FIG. 8 is the portion of the graphical representation of FIG. 6 annotated to identify a diagnostic window according to an embodiment of the present disclosure.

Referring now to FIGS. 5-8, shown therein are graphical representations of diagnostic information illustrating aspects of an embodiment of the present disclosure. In that regard, FIG. 5 is a graphical representation of measured pressure, velocity, and resistance within a vessel; FIG. 6 is a magnified view of a portion of the graphical representation of FIG. 5 corresponding to a resting state of a patient; FIG. 7 is a magnified view of a portion of the graphical representation of FIG. 5 corresponding to a hyperemic state of a patient; and FIG. 8 is the portion of the graphical representation of FIG. 6 annotated to identify a diagnostic window according to an embodiment of the present disclosure.

Referring more particularly to FIG. 5, shown therein is a graphical representation 180 of diagnostic information pertaining to a vessel. More specifically, the graphical representation 180 includes a graph 182 plotting pressure within the vessel over time, a graph 184 plotting velocity of the fluid within the vessel over time, and a graph 186 plotting resistance within the vessel over time. In that regard, the resistance (or impedance) shown in graph 186 is calculated based on the pressure and velocity data of graphs 182 and 184. In particular, the resistance values shown in graph 186 are determined by dividing the pressure measurement of graph 182 by the velocity measurement 184 for the corresponding point in time. The graphical representation 180 includes a time period 188 that corresponds to a resting state of the patient's heart and a time period 190 that corresponds to a stressed state of the patient's heart. In that regard, the stressed state of the patient's heart is caused by the administration of a hyperemic agent in some instances.

To better illustrate the differences in the pressure, velocity, and resistance data between the resting and stressed states of the patient, close-up views of the data within windows 192 and 194 are provided in FIGS. 6 and 7. Referring more specifically to FIG. 6, window 192 of the graphical representation 180 includes graph portions 196, 198, and 200 that correspond to graphs 182, 184, and 186, respectively. As shown, in the resting state of FIG. 6, the resistance within the vessel has an average value of approximately 0.35 on the scale of graph 200, as indicated by line 202. Referring now to FIG. 7, window 194 of the graphical representation 180 includes graph portions 204, 206, and 208 that correspond to graphs 182, 184, and 186, respectively. As shown, in the stressed state of FIG. 7, the resistance within the vessel is significantly less than the resting state with a value of approximately 0.20 on the scale of graph 208, as indicated by line 210. As current FFR techniques rely on the average pressures across an entire heartbeat cycle, it is necessary to stress the patient's heart to achieve this reduced and relatively constant resistance across the entire heartbeat so that the data obtained is suitable for use with FFR techniques.

Referring to FIG. 8, similar to FIG. 6 window 192 of the graphical representation 180 of FIG. 5 is shown and includes graph portions 196, 198, and 200 that correspond to graphs 182, 184, and 186, respectively. However, in FIG. 8 a section 212 of the heartbeat cycle of the patient has been identified. As shown, section 212 corresponds to the portion of the heartbeat cycle of the patient where the resistance is reduced without the use of a hyperemic agent or other stressing technique. That is, section 212 is a portion of the heartbeat cycle of a resting patient that has a naturally reduced and relatively constant resistance. In other instances, section 212 of the heartbeat cycle encompasses the portion the heartbeat cycle that is less than a fixed percentage of the maximum resistance of the heartbeat cycle. In that regard, the fixed percentage of the maximum resistance of the heartbeat cycle is less than 50%, less than 30%, less than 25%, less than 20%, less than 15%, less than 10%, and less than 5% in some embodiments. In yet other instances, section 212 of the heartbeat cycle encompasses the portion the heartbeat cycle that is less than a fixed percentage of the average resistance of the heartbeat cycle. In that regard, the fixed percentage of the average resistance of the heartbeat cycle is less than 75%, less than 50%, less than 25%, less than 20%, less than 15%, less than 10%, and less than 5% in some embodiments.

Accordingly, in some embodiments of the present disclosure, the portion of the heartbeat cycle coinciding with section 212 is utilized as a diagnostic window for evaluating a stenosis of the vessel of a patient without the use of a hyperemic agent or other stressing of the patient's heart. In particular, the pressure ratio (distal pressure divided by proximal pressure) across the stenosis is calculated for the time period corresponding to section 212 for one or more heartbeats. The calculated pressure ratio is an average over the diagnostic window defined by section 212 in some instances. By comparing the calculated pressure ratio to a threshold or predetermined value, a physician or other treating medical personnel can determine what, if any, treatment should be administered. In that regard, in some instances, a calculated pressure ratio above a threshold value (e.g., 0.80 on a scale of 0.00 to 1.00) is indicative of a first treatment mode (e.g., no treatment, drug therapy, etc.), while a calculated pressure ratio below the threshold value is indicative of a second, more invasive treatment mode (e.g., angioplasty, stent, etc.). In some instances, the threshold value is a fixed, preset value. In other instances, the threshold value is selected for a particular patient and/or a particular stenosis of a patient. In that regard, the threshold value for a particular patient may be based on one or more of empirical data, patient characteristics, patient history, physician preference, available treatment options, and/or other parameters.

In some instances, section 212 is identified by monitoring pressure and fluid flow velocity within the vessel using one or more instruments and calculating the resistance within the vessel based on the measured pressure and velocity. For example, referring again to the embodiment of FIG. 3, in some instances the instrument 130 includes one or more sensing elements configured to monitor at least pressure and flow velocity, while instrument 132 includes one or more sensing elements configured to monitor at least pressure. Accordingly, with the one or more sensing elements of instrument 130 positioned distal of the stenosis and the one or more sensing elements of instrument 132 positioned proximal of the stenosis, the pressure and flow velocity measurements obtained by instrument 130 are utilized to identify section 212. Based on the identification of section 212, then the corresponding distal pressure measurements (as obtained by the one or more sensing elements of instrument 130) are compared to the proximal pressure measurements (as obtained by the one or more sensing elements of instrument 132) to calculate the pressure ratio across the stenosis during the diagnostic window defined by section 212. Additional examples of evaluating a vessel based on pressure and flow velocity measurements are described in UK Patent Application No. 1003964.2, filed Mar. 10, 2010 and titled "METHOD AND APPARATUS FOR THE MEASUREMENT OF A FLUID FLOW RESTRICTION IN A VESSEL", which is hereby incorporated by reference in its entirety.

In other instances, section 212 is identified without monitoring fluid velocity. In that regard, several techniques for identifying suitable diagnostic windows for use in evaluating a stenosis of a vessel based on pressure ratio across the stenosis without the use of hyperemic agents are described in U.S. patent application Ser. No. 13/460,296, filed Apr. 30, 2012 and titled "DEVICES, SYSTEMS, AND METHODS FOR ASSESSING A VESSEL," which is hereby incorporated by reference in its entirety. In some instances, the diagnostic window is identified solely based on characteristics of the pressure measurements obtained by instruments positioned within the vessel. Accordingly, in such instances, the instruments utilized need only have elements configured to monitor a pressure within the vessel, which results in reduced cost and simplification of the system. Exemplary techniques for evaluating a vessel based on pressure measurements are described in UK Patent Application No. 1100137.7, filed Jan. 6, 2011 and titled "APPARATUS AND METHOD OF ASSESSING A NARROWING IN A FLUID FILLED TUBE" and UK Patent Application No. 1100136.9, filed Jan. 6, 2011 and titled "APPARATUS AND METHOD OF CHARACTERIZING A NARROWING IN A FLUID FILLED TUBE," each of which is hereby incorporated by reference in its entirety.

In general, the diagnostic window for evaluating differential pressure across a stenosis without the use of a hyperemic agent in accordance with the present disclosure may be identified based on characteristics and/or components of one or more of proximal pressure measurements, distal pressure measurements, proximal velocity measurements, distal velocity measurements, ECG waveforms, and/or other identifiable and/or measurable aspects of vessel performance. In that regard, various signal processing and/or computational techniques can be applied to the characteristics and/or components of one or more of proximal pressure measurements, distal pressure measurements, proximal velocity measurements, distal velocity measurements, ECG waveforms, and/or other identifiable and/or measurable aspects of vessel performance to identify a suitable diagnostic window.

In some embodiments, the determination of the diagnostic window and/or the calculation of the pressure differential are performed in approximately real time or live to identify the section 212 and calculate the pressure ratio. In that regard, calculating the pressure ratio in "real time" or "live" within the context of the present disclosure is understood to encompass calculations that occur within 10 seconds of data acquisition. It is recognized, however, that often "real time" or "live" calculations are performed within 1 second of data acquisition. In some instances, the "real time" or "live" calculations are performed concurrent with data acquisition. In some instances the calculations are performed by a processor in the delays between data acquisitions. For example, if data is acquired from the pressure sensing devices for 1 ms every 5 ms, then in the 4 ms between data acquisitions the processor can perform the calculations. It is understood that these timings are for example only and that data acquisition rates, processing times, and/or other parameters surrounding the calculations will vary. In other embodiments, the pressure ratio calculation is performed 10 or more seconds after data acquisition. For example, in some embodiments, the data utilized to identify the diagnostic window and/or calculate the pressure ratio are stored for later analysis.

Because the pressure ratio can be calculated based on a single cardiac cycle in accordance with the present disclosure, a real-time or live pressure ratio calculation can made while the distal pressure measuring device is moved through the vessel (e.g., during a pullback). Accordingly, in some instances the system includes at least two modes: a single-cardiac-cycle mode that facilitates pressure ratio calculations while moving the distal pressure measuring device through the vessel and a multi-cardiac-cycle mode that provides a more precise pressure ratio calculation at a discrete location. In one embodiment of such a system, the software user interface is configured to provide the live pressure ratio value until the distal pressure measuring device is moved to the desired location and a measurement button is selected and/or some other actuation step is taken to trigger the multi-cardiac-cycle mode calculation.

Figure 9:
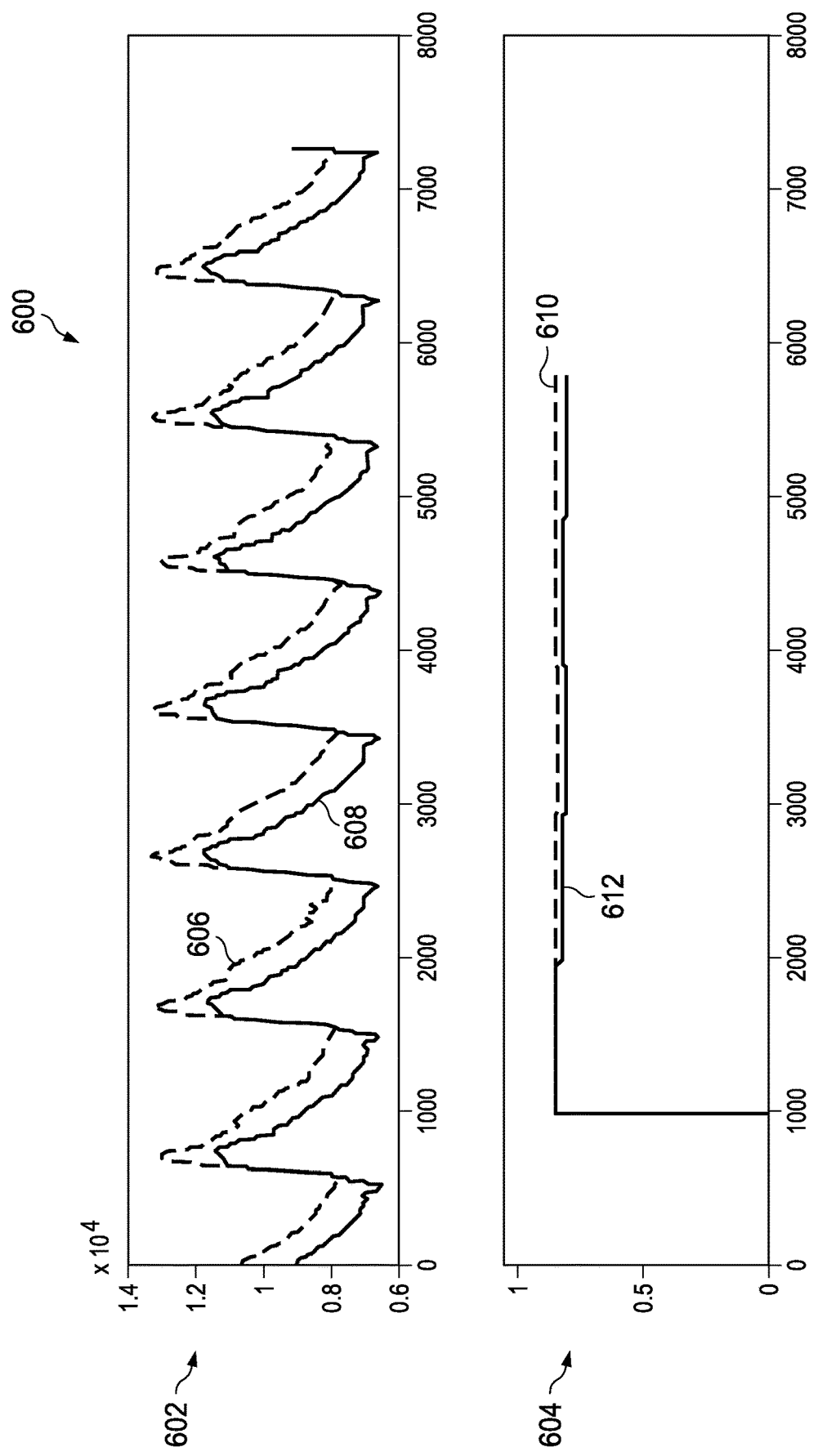
FIG. 9 is a pair of graphical representations, where the top graphical representation illustrates proximal and distal pressure measurements within a vessel and the bottom graphical representation illustrates a ratio of the proximal and distal pressure measurements and a fit between the proximal pressure waveform and the distal pressure waveform according to an embodiment of the present disclosure.
Figure 10:
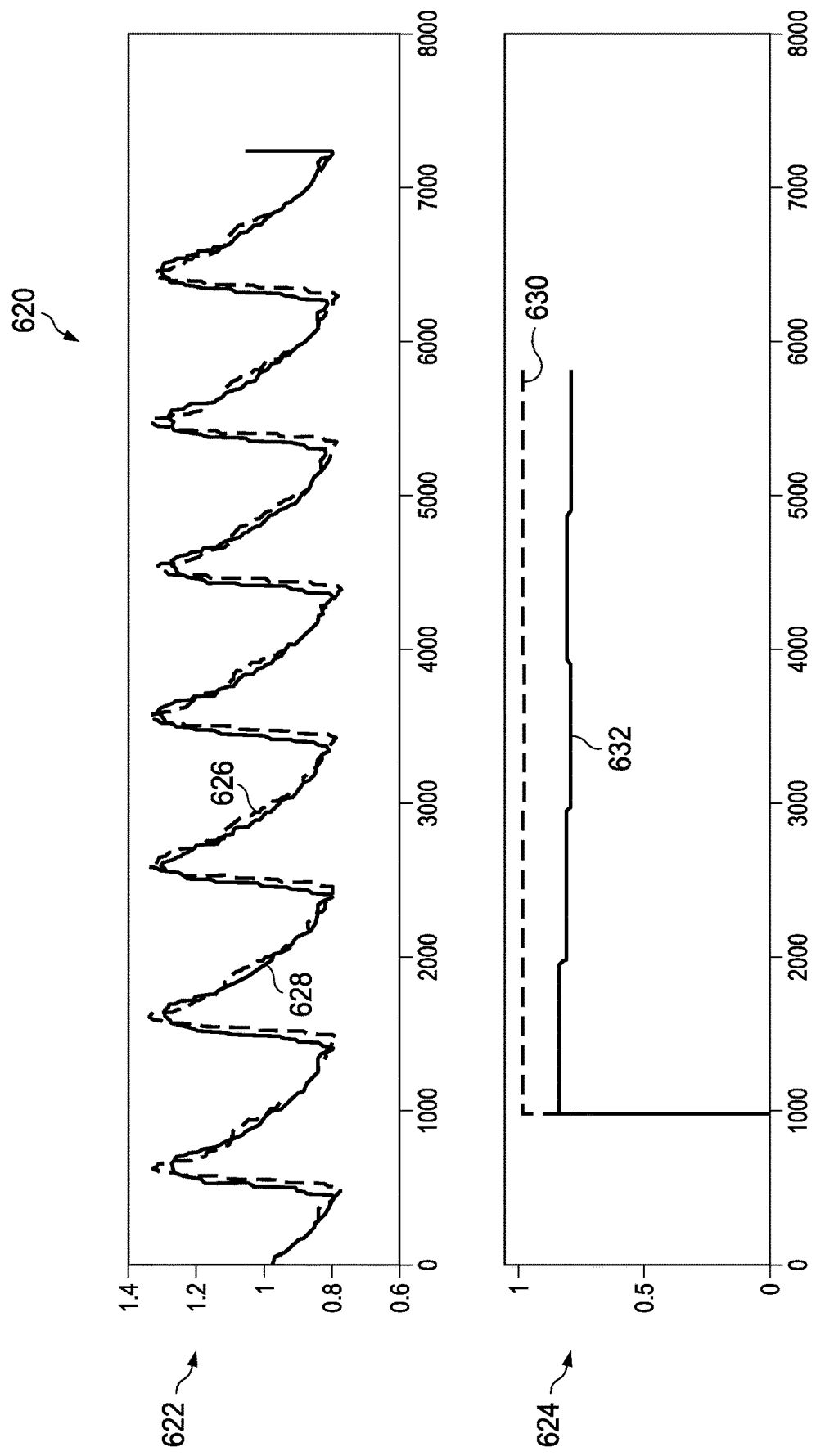
FIG. 10 is a pair of graphical representations similar to that of FIG. 9, but where the distal pressure measurement waveform of the top graphical representation has been shifted relative the distal pressure waveform of FIG. 9 and the bottom graphical representation illustrates the corresponding ratio of the proximal and distal pressure measurements and the fit between the proximal pressure waveform and the distal pressure waveform based on the shifted distal pressure measurement waveform.

Referring now to FIGS. 9 and 10, shown therein are aspects of a technique for evaluating a vessel according to another embodiment of the present disclosure. In that regard, the technique described below with respect to FIGS. 9 and 10 may be implemented using any of the diagnostic windows and associated techniques discussed above for evaluating a vessel using a pressure ratio across a lesion, stenosis, or region of interest. However, as will be discussed in greater detail, the technique associated with FIGS. 9 and 10 is not dependent upon the accuracy of the pressure measurements to evaluate the stenosis. Accordingly, concerns about pressure transducer drift during a procedure are largely reduced or eliminated by this technique. Further, the need to repeatedly calibrate or normalize the distal pressure measurement device to the proximal pressure measurement device during a procedure is likewise reduced or eliminated.

In some instances, embodiments of the present disclosure are configured to avoid and/or account for issues associated with variations in pressure measurements of one instrument relative to another over time, which is commonly referred to as drift. In that regard, a major source of drift in traditional Fractional Flow Reserve (FFR) measurements is divergence in the pressure reading of a guidewire relative to the pressure reading of a guide catheter. In that regard, because FFR is calculated as the ratio of the pressure measurement obtained by the guidewire to the pressure measurement obtained by the catheter, this divergence has an impact on the resulting FFR value.

Referring initially to FIG. 9, shown therein is a graphical representation 600 illustrating aspects of the technique for evaluating a vessel according to the current embodiment of the present disclosure. As shown, the graphical representation 600 includes a graph 602 and a graph 604. Graph 602 illustrates a proximal pressure waveform 606 and a distal pressure waveform 608 of a patient over time. Graph 604, in turn, illustrates corresponding calculations based on those waveforms 606 and 608. In that regard, plot 610 is representative of a pressure ratio of the distal pressure waveform 608 relative to the proximal pressure waveform 606 over time, which in some embodiments is during a wave free period of the heartbeat cycle. Plot 610 is representative of the pressure ratio calculation used in some of the vessel evaluation techniques described above. Plot 612 is representative of a slope comparison between the distal pressure waveform 608 and the proximal pressure waveform 606. In that regard, the slope of the distal pressure waveform 608 is compared to the slope of the proximal pressure waveform 606 to provide an indication of the severity of a lesion or stenosis. In some instances, a best fit regression slope is utilized. In that regard, one or more of polynomial fitting, multiple line regression, estimation of the slope from points at either end of the waveforms, and/or other suitable fitting techniques are utilized. Further, the fitting may be performed over a single heartbeat or over multiple heartbeat cycles. When the slope of the distal pressure waveform 608 is equal to the slope of the proximal pressure waveform 606, then the polyfit regression slope (i.e., a slope obtained through polynomial curve fitting) will be equal to 1.0, which is indicative of no lesion or stenosis. On the other hand, as the slope of the distal pressure waveform 608 diverges from the slope of the proximal pressure waveform 606, then the polyfit regression slope move towards 0.0, which is indicative of a severe lesion or stenosis (e.g., total occlusion or severe blockage). Accordingly, the severity of the lesion or stenosis can be evaluated based on the polyfit regression slope. More specifically, the closer the polyfit regression slope is to 1.0 the less severe the lesion/stenosis and the closer the polyfit regression slope is to 0.0 the more severe the lesion/stenosis. Similar to the 0.80 cutoff for pressure ratios discussed above, a predetermined threshold value can be utilized for the regression slope comparison. For example, in some instances, the predetermined threshold value is between about 0.70 and about 0.90, with some particular embodiments using a threshold value of 0.75, 0.80, 0.85, or otherwise. In other instances, the predetermined threshold value is less than 0.70 or greater than 0.90.

As noted above, this slope-based technique is not dependent upon the accuracy of the pressure measurements to evaluate the stenosis. In that regard, FIG. 10 illustrates this point. Shown therein is a graphical representation 620 that includes a graph 622 and a graph 624. Graph 622 illustrates a proximal pressure waveform 626 and a distal pressure waveform 628 of a patient over time. In that regard, proximal pressure waveform 626 is the same as proximal pressure waveform 606 of FIG. 9 and distal pressure waveform 628 is substantially the same as distal pressure waveform 608 of FIG. 9, but to illustrate the effects of transducer drift the distal pressure waveform 628 has been increased by a constant value of 10 mmHg compared to distal pressure waveform 608. Graph 624 illustrates corresponding calculations based on those waveforms 626 and 628. In that regard, plot 630 is representative of a pressure ratio of the distal pressure waveform 628 relative to the proximal pressure waveform 626 over time. Notably, the values of plot 630 are substantially increased relative to the values of plot 610 of FIG. 9. This illustrates one of the potential problems of an inaccurate and/or non-normalized distal pressure measurement in the context of the pressure ratio calculation. On the other hand, plot 632 is representative of a slope comparison between the distal pressure waveform 628 and the proximal pressure waveform 626. As shown, plot 632 substantially matches plot 612 of FIG. 9. This is because plots 612 and 632 are based upon the shape of the proximal and distal waveforms, which are the same between FIGS. 9 and 10. In that regard, the distal pressure waveform 628 has the same shape as distal pressure waveform 608, but has simply been shifted upward by a value of 10 mmHg. As a result, plots 612 and 632 based on the slopes of the waveforms are pressure-value independent and, therefore, drift independent. It is understood that this waveform shape and/or waveform slope based technique can be implemented using the waveforms from any of the diagnostic windows discussed above.

Figure 11:
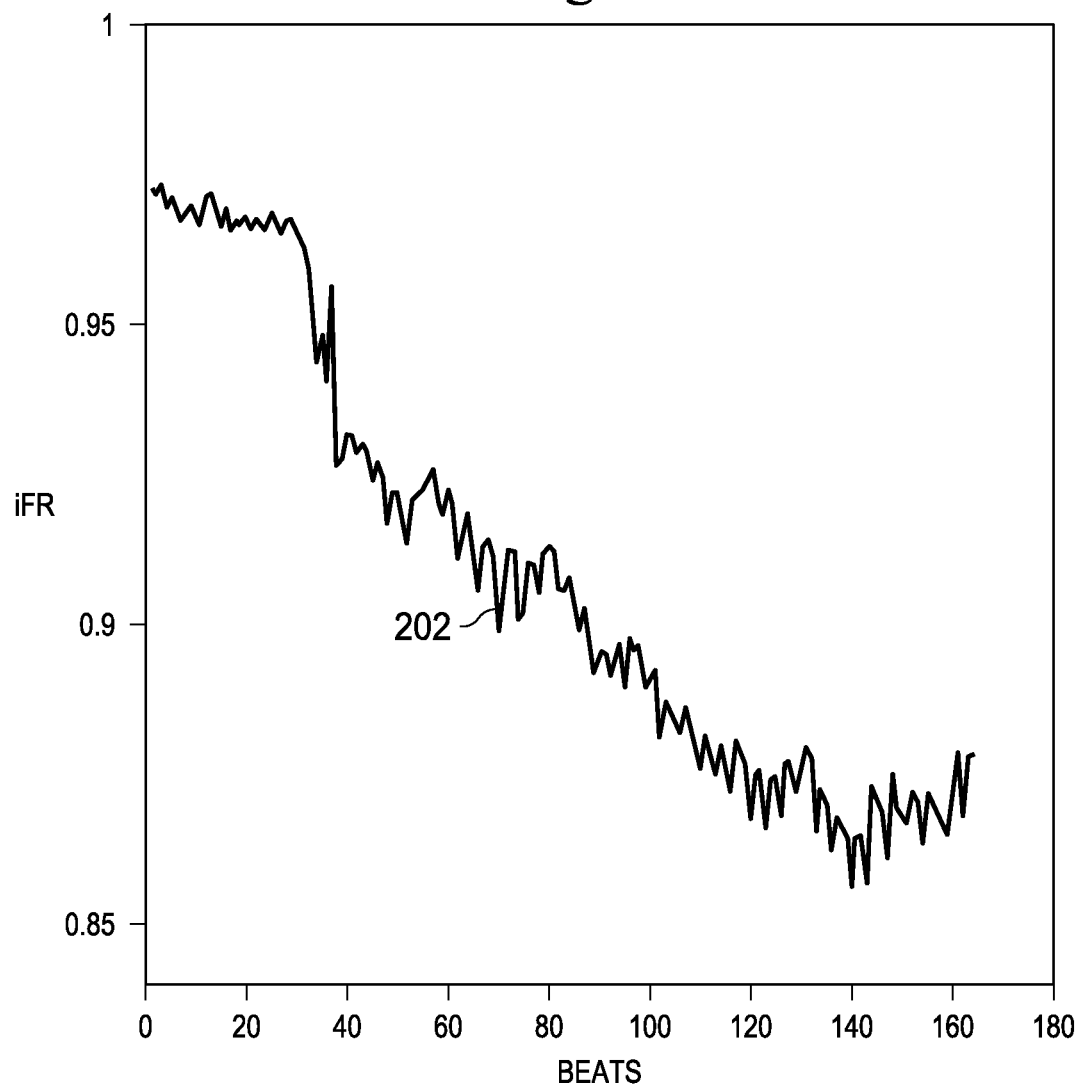
FIG. 11 is a graphical representation of pressure measurements obtained from within a vessel according to an embodiment of the present disclosure.
Figure 12:
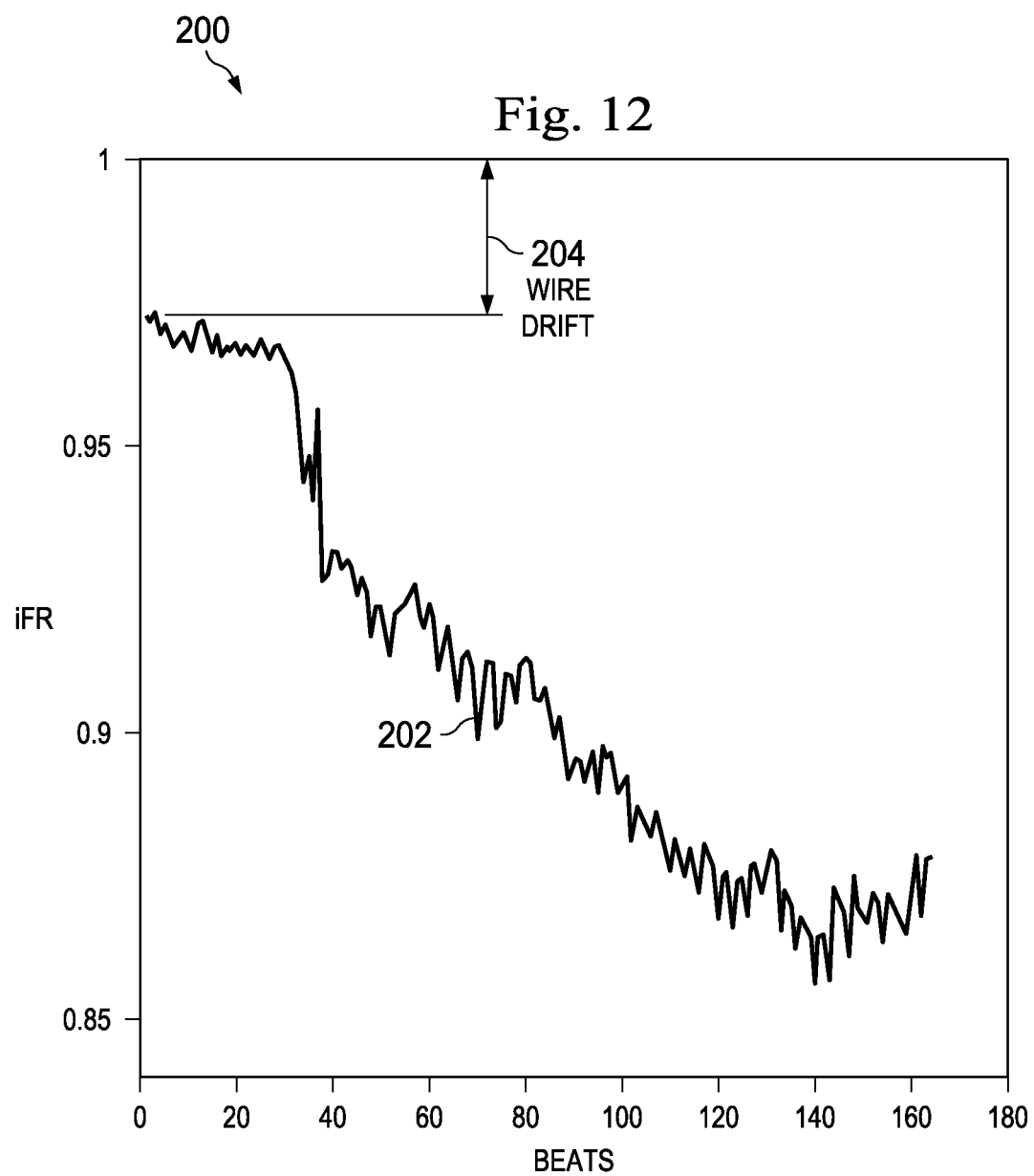
FIG. 12 is a graphical representation of pressure measurements obtained from within a vessel similar to FIG. 11, but showing an offset resulting from instrument drift according to an embodiment of the present disclosure.
Figure 13:
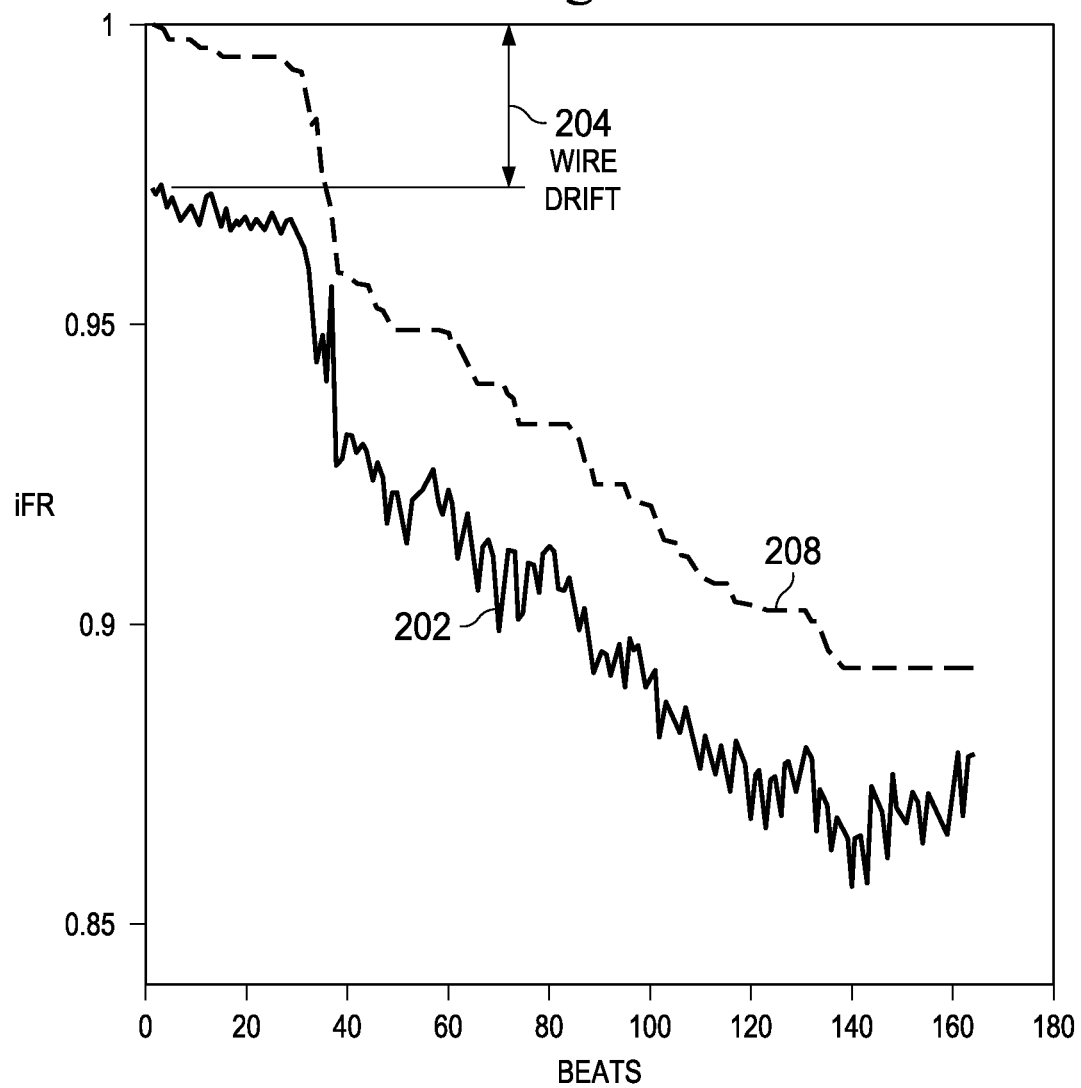
FIG. 13 is a graphical representation of pressure measurements obtained from within a vessel similar to FIGS. 11 and 12, but showing a modified plot accounting for the offset resulting from the instrument drift according to an embodiment of the present disclosure.

Referring now to FIGS. 11-13, shown therein are aspects of a technique for evaluating a vessel according to another embodiment of the present disclosure. In that regard, the technique described below with respect to FIGS. 11-13 may be implemented using any of the diagnostic windows and associated techniques discussed above for evaluating a vessel using a pressure ratio across a lesion, stenosis, or region of interest. However, as will be discussed in greater detail, the technique associated with FIGS. 11-13 automatically corrects the diagnostic measurements to account for drift in the pressure measurements obtained by a pressure sensing guidewire moved through the vessel. Accordingly, concerns about pressure transducer drift during a procedure are largely reduced or eliminated by this technique.

Referring initially to FIG. 11, shown therein is a graph 200 mapping a pressure ratio value calculated using a diagnostic window in accordance with the present disclosure, which may be referred to as "iFR" in the drawings, relative to heartbeats of a patient as a first instrument is moved through a vessel relative to a second instrument, including across at least one stenosis of the vessel. In that regard, the second instrument is maintained in a position proximal of the at least one stenosis while the first instrument is moved from a position distal of the at least one stenosis to a position proximal of the at least one stenosis and adjacent the second instrument or vice versa (i.e., the first instrument is moved from a position proximal of the at least one stenosis and adjacent the second instrument to a position distal of the at least one stenosis). In the illustrated embodiment of FIG. 11, the relative position of the first instrument as depicted in plot 202 transitions from proximal to distal as the plot 202 extends from left to right.

Since plot 202 represents the pressure ratio between the first and second instruments, the pressure ratio should be equal to 1.0 when the first and second instruments are positioned adjacent to one another proximal of the at least one stenosis. However, as shown in FIG. 12, even at the proximal most positioning of the first instrument (depicted on the far left side of the graph 200), the ratio is less than 1.0. More specifically, there is a difference 204 between the maximum pressure ratio as depicted by plot 202 and the expected maximum pressure ratio of 1.0. This difference 204 is attributable to drift in the pressure measurements between the first and second instruments in some instances. While the maximum pressure ratio is illustrated as being less than 1.0, in other instances drift causes the pressure ratio to be greater than 1.0. To get the most accurate diagnosis and determine the most appropriate treatment option(s) for the patient, the difference 204 is accounted for in some instances.

In that regard, the difference 204 can be accounted for in several different ways. In one embodiment, a fixed value equal to the difference 204 is added to all of the pressure ratio measurements depicted by plot 202. In other words, the plot 202 is stepped up (or down) to account for the difference 204. In other embodiments, a variable value is added to the pressure ratio measurements depicted by plot 202 based on when the underlying measurements were obtained. In that regard, in some procedures the first and second instruments will be normalized with respect to each other at a first point in time. Subsequently, the first instrument will be moved through the vessel and the pressure measurements utilized to create plot 202 will be obtained. Based on the obtained pressure measurements, the difference 204 is determined.

In some implementations, after the first instrument has been moved through the vessel and the pressure measurements have been obtained, the first and second instruments will be normalized with respect to each other again at a second point in time in order to determine the difference 204. To that end, in some instances confirmation of the first and second instruments being positioned adjacent to one another in a manner suitable for normalization is performed manually (by the user) and/or automatically (by the system). For example, in some implementations the positions of the first and/or second instruments are co-registered with angiographic images of the vessel such that the system can automatically detect that the first and second instruments are within a threshold distance from one another suitable for normalization. Upon such detection, the system may automatically re-normalize the first and second instruments and/or prompt a user that the instruments are in a suitable position for normalization such that the user can determine whether to have the system normalize the first and second instruments at that time or not. Alternatively, the user can simply visualize the relative positions of the first and second instruments and actuate the system (e.g., by pushing a physical button or a virtual button on a graphical user interface of the system) to cause the first and second instruments to be normalized to one another. In some instances, the system will provide a warning or alert to the user if the user attempts to normalize the first and second instruments, but the system detects that the first and second instruments are not in close enough proximity for normalization.

In some instances, the amount of time elapsed between when the first and second instruments were first normalized with respect to each other and when the proximal pressure measurements were obtained (i.e., the measurements expected to have a ratio of 1.0) and/or when the first and second instruments are normalized with respect to each other again is utilized to calculate the different values to be added to the pressure ratio measurements depicted by plot 202. For example, in some instances the drift is assumed to have occurred linearly over time between when the first and second instruments were normalized with respect to each other and when the proximal pressure measurements were obtained (i.e., the measurements expected to have a ratio of 1.0) such that pressure ratios based on the earlier obtained pressure measurements will have less adjustment than those based on the later obtained pressure measurements. In other instances, drift is assumed to have occurred in a non-linear fashion and corresponding non-linear calculations are utilized to determine the appropriate adjustments to the pressure ratio measurements depicted by plot 202. Further, in some instances the first and/or second instrument will have known drift characteristics (determined from empirical studies or otherwise) that can be utilized to determine the values to be added to the pressure ratio measurements depicted by plot 202. Generally, any suitable mathematical techniques can be utilized to account for the difference 204 attributable to drift.

Referring now to FIG. 13, shown therein is a graph 206 depicting both original plot 202 and an adjusted plot 208. In that regard, adjusted plot 208 accounts for the difference 204 utilizing one or more of the techniques described above. Further, plot 208 has been smoothed to remove artifacts and/or noise present in plot 202. More specifically, plot 208 has been constrained such that the pressure ratios are equal to or larger than the pressure ratios for positions more distal and equal to or smaller than the pressure ratios for positions more proximal. For example, if the first instrument is pulled back from a position distal of the at least one stenosis to a position proximal of the at least one stenosis, then the corresponding pressure ratios should only increase over time as the first instrument is moved proximally. Plot 208 illustrates such an approach where the values on the far right hand side of the graph represent the first instrument being positioned distal of the at least one stenosis. Similarly, if the first instrument is advanced from a position proximal of the at least one stenosis to a position distal of the at least one stenosis, then the corresponding pressure ratios should only decrease over time as the first instrument is moved distally. Plot 208 illustrates such an approach where the values on the far left hand side of the graph represent the first instrument being positioned proximal of the at least one stenosis.

As shown in FIG. 13, plot 208 can be shown along with plot 202 to provide a user with an indication of the amount of drift correction and/or other conditioning of the pressure ratio data. In some instances, the user interface of the system displays numerically, textually, graphically, and/or otherwise the correction(s) and/or conditioning applied to the pressure ratio data. To that end, in some implementations the user is able to accept or deny the correction(s) and/or conditioning. Further, in some implementations one or more predetermined thresholds are set by the system and/or the user such that if the correction(s) and/or conditioning exceed the thresholds an alert is provided. The alert suggests remeasurement in some instances. In some implementations, the plot 208 is automatically calculated and displayed by the system. In other instances, a user provides an input to the system to cause the plot 208 and/or other correction/conditioning information to be displayed.

Figure 14:
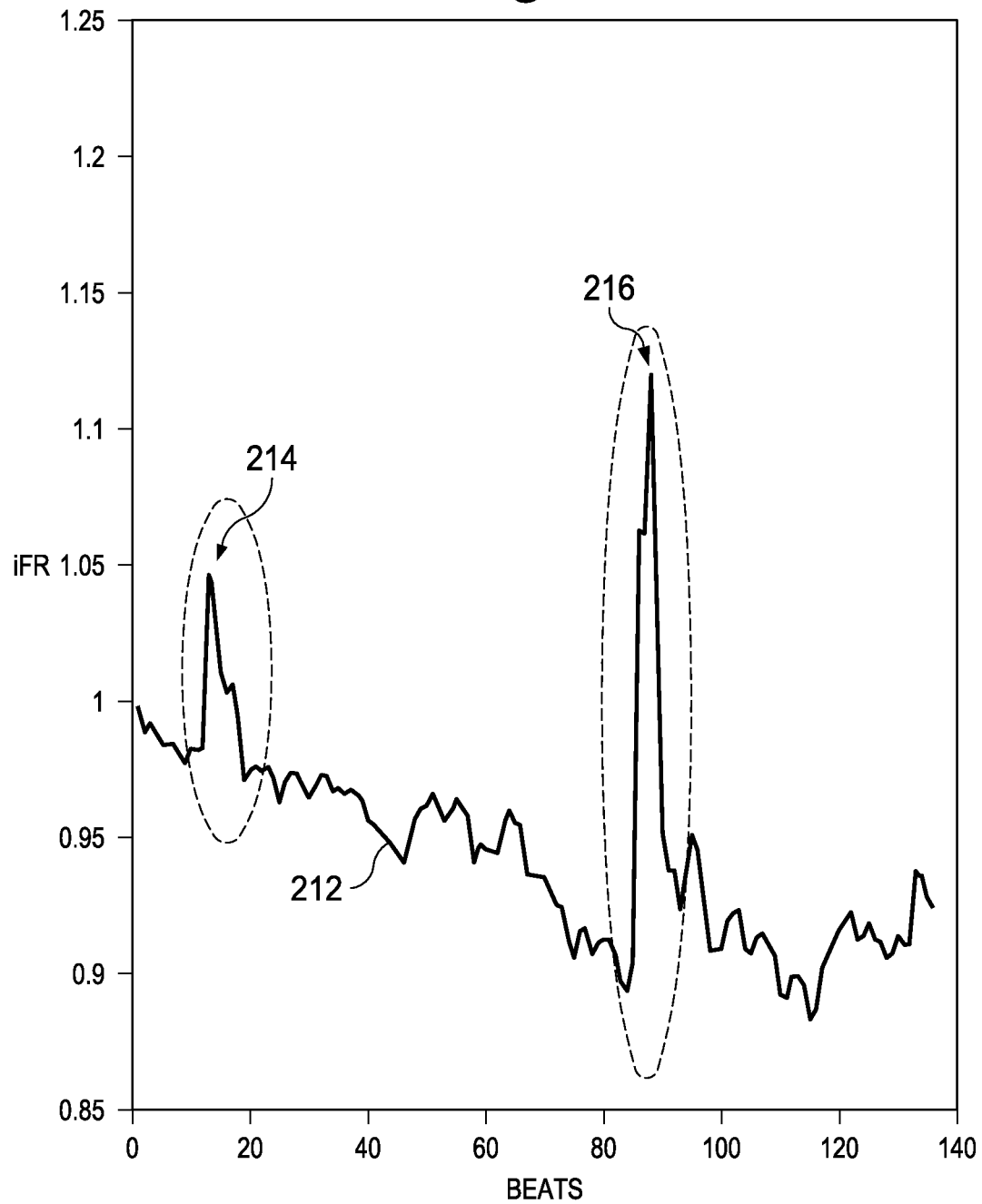
FIG. 14 is a graphical representation of pressure measurements obtained from within a vessel having disruptions in the pressure measurements according to an embodiment of the present disclosure.

Referring now to FIGS. 14-18, shown therein are aspects of techniques for conditioning pressure ratio data according to embodiments of the present disclosure. More specifically, FIGS. 14-18 illustrate techniques for removing noise/irregularities from pressure ratio data. Referring initially to FIG. 14, shown therein is a graph 210 mapping a pressure ratio value calculated using a diagnostic window in accordance with the present disclosure, which may be referred to as "iFR" in the drawings, relative to heartbeats of a patient as a first instrument is moved through a vessel relative to a second instrument, including across at least one stenosis of the vessel. In that regard, the second instrument is maintained in a position proximal of the at least one stenosis while the first instrument is moved from a position distal of the at least one stenosis to a position proximal of the at least one stenosis and adjacent the second instrument or vice versa (i.e., the first instrument is moved from a position proximal of the at least one stenosis and adjacent the second instrument to a position distal of the at least one stenosis). In the illustrated embodiment of FIG. 14, the relative position of the first instrument as depicted in plot 212 transitions from proximal to distal as the plot 212 extends from left to right.

As shown, the plot 212 includes a peak 214 and a peak 216 that greatly exceed the maximum expected pressure ratio of 1.0. In that regard, these pressure peaks 214, 216 are indicative of noise, interference, physiological effects (e.g., a patient moving or coughing), and/or other disruption in the pressure measurements. Accordingly, it is desirable to remove these disruptions from the pressure ratio plot 212. To that end, FIG. 15 provides a graph 218 depicting both original plot 212 and an adjusted plot 220. In that regard, adjusted plot 220 removes the effects of the peaks 214 and 216 from the pressure ratio calculations. To that end, any suitable filtering technique may be utilized. For example, in the illustrated embodiment plot 220 has been smoothed to remove the peaks 214 and 216 along with other artifacts and/or noise present in plot 212. For example, plot 220 has been constrained such that the pressure ratios are equal to or larger than the pressure ratios for positions more distal and equal to or smaller than the pressure ratios for positions more proximal. Generally, any suitable processing techniques can be utilized to remove the effects of peaks 214 and 216 and smooth the overall plot of the pressure ratios.

Referring now to FIG. 16, shown therein is a graph 230 mapping a pressure ratio value calculated using a diagnostic window in accordance with the present disclosure, which may be referred to as "iFR" in the drawings, relative to heartbeats of a patient as a first instrument is moved through a vessel relative to a second instrument, including across at least one stenosis of the vessel. In that regard, the second instrument is maintained in a position proximal of the at least one stenosis while the first instrument is moved from a position distal of the at least one stenosis to a position proximal of the at least one stenosis and adjacent the second instrument or vice versa (i.e., the first instrument is moved from a position proximal of the at least one stenosis and adjacent the second instrument to a position distal of the at least one stenosis). In the illustrated embodiment of FIG. 16, the relative position of the first instrument as depicted in plot 232 transitions from proximal to distal as the plot 232 extends from left to right.

As shown, the plot 232 includes a plurality of peaks 234 that greatly exceed the maximum expected pressure ratio of 1.0. In that regard, these pressure peaks 234 are indicative of physiological effects and, in particular, a patient coughing during the procedure. Accordingly, it is desirable to remove these disruptions from the pressure ratio plot 232. To that end, FIG. 17 provides a graph 236 depicting both original plot 232 and an adjusted plot 238. In that regard, adjusted plot 238 removes the effects of the peaks 234 associated with the patient coughing from the pressure ratio calculations. To that end, any suitable filtering technique may be utilized. For example, in the illustrated embodiment plot 238 has been smoothed to remove the peaks 234 along with other artifacts and/or noise present in plot 232. For example, plot 238 has been constrained such that the pressure ratios are equal to or larger than the pressure ratios for positions more distal and equal to or smaller than the pressure ratios for positions more proximal. Generally, any suitable processing techniques can be utilized to remove the effects of peaks 234 and smooth the overall plot of the pressure ratios. FIG. 18 provides a graph 240 similar to that of FIG. 17, but also showing a plot 242 of the pressure measurements obtained by the first and second instruments along with the plots 232 (original pressure ratio measurements) and 238 (filtered/conditioned pressure ratio measurements).

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of evaluating a vessel of a patient, comprising:
   equalizing, by a computing device, a pressure sensing intravascular catheter within the vessel to a pressure sensing intravascular guidewire within the vessel, the pressure sensing intravascular guidewire comprising a shaft having a proximal portion, a distal portion positioned within the vessel, and a pressure transducer coupled to the distal portion;
   obtaining, by the computing device after the equalizing, first pressure measurements from the pressure sensing intravascular catheter at a position proximal of a stenosis of the vessel;
   obtaining, by the computing device after the equalizing, second pressure measurements from the pressure transducer of the pressure sensing intravascular guidewire as the pressure sensing intravascular guidewire is moved from a position distal of the stenosis to a position proximal of the stenosis;
   determining, by the computing device, an offset between a measured pressure ratio and an expected pressure ratio, wherein the measured pressure ratio comprises a ratio between a pressure measurement of the first pressure measurements and a pressure measurement of the second pressure measurements, and the pressure measurement of the second pressure measurement is obtained with the pressure transducer of the pressure sensing intravascular guidewire positioned proximal of the stenosis after the pressure sensing intravascular guidewire is moved from the position distal of the stenosis to the position proximal of the stenosis;
   calculating, by the computing device, a plurality of pressure ratios between the second pressure measurements from the pressure transducer of the pressure sensing intravascular guidewire and the first pressure measurements from the pressure sensing intravascular catheter, wherein the step of calculating the pressure ratios includes:
      determining, for each of the plurality of pressure ratios, a respective value of a series of linearly increasing values based on the equalizing and the offset, wherein the respective value of the series of linearly increasing values is associated with a respective time elapsed between when the pressure sensing intravascular guidewire and the pressure sensing intravascular catheter were equalized to each other and when pressure measurements used for calculating the pressure ratio were obtained; and automatically correcting for the determined offset by adding the series of linearly increasing values to the plurality of pressure ratios such that the respective value of the series of linearly increasing values is added to each corresponding pressure ratio of the plurality of pressure ratios, wherein automatically correcting for the determined offset comprises automatically correcting for a drift between the first pressure measurements from the pressure sensing intravascular catheter and the second pressure measurements from the pressure transducer of the pressure sensing intravascular guidewire; and outputting, by the computing device, the calculated pressure ratios to a display.

2. The method of claim 1, wherein the values added to the pressure ratios increase non-linearly over time.

3. The method of claim 1, wherein the calculated pressure ratios are constrained such that the pressure ratios increase in correspondence with the pressure sensing intravascular guidewire moving from the position distal of the stenosis to the position proximal of the stenosis.

4. The system of claim 1, wherein the expected pressure ratio is 1.

5. A system comprising:
a pressure sensing intravascular guidewire, the pressure sensing intravascular guidewire comprising a shaft having a proximal portion, a distal portion sized and shaped to be positioned within a vessel of a patient, and a pressure transducer coupled to the distal portion; and
a computing device configured for communication with the pressure sensing intravascular guidewire and a pressure sensing intravascular catheter, the computing device configured to:
equalize the pressure sensing intravascular catheter to the pressure sensing intravascular guidewire;
obtain, after equalization, first pressure measurements from the pressure sensing intravascular catheter within a vessel at a position proximal of a stenosis of the vessel;
obtain, after equalization, second pressure measurements with the pressure transducer of the pressure sensing intravascular guidewire within the vessel as the pressure sensing intravascular guidewire is moved from a position distal of the stenosis to a position proximal of the stenosis;
determine an offset between a measured pressure ratio and an expected pressure ratio, wherein the measured pressure ratio comprises a ratio between a pressure measurement of the first pressure measurements and a pressure measurement of the second pressure measurements, and the pressure measurement of the second pressure measurement is obtained with the pressure transducer of the pressure sensing intravascular guidewire positioned proximal of the stenosis after the pressure sensing intravascular guidewire is moved from the position distal of the stenosis to the position proximal of the stenosis;
calculate a plurality of pressure ratios between the second pressure measurements from the pressure transducer of the pressure sensing intravascular guidewire and the first pressure measurements from the pressure sensing intravascular catheter, wherein the step of calculating the pressure ratios includes:

determining, for each of the plurality of pressure ratios, a respective value of a series of linearly increasing values based on the equalizing and the offset, wherein the respective value of the series of linearly increasing values is associated with a respective time elapsed between when the pressure sensing intravascular guidewire and the pressure sensing intravascular catheter were equalized to each other and when pressure measurements used for calculating the pressure ratio were obtained; and automatically correcting for the determined offset by adding the series of linearly increasing values to the plurality of pressure ratios such that the respective value of the series of linearly increasing values is added to each corresponding pressure ratio of the plurality of pressure ratios pressure ratios, wherein automatically correcting for the determined offset comprises automatically correcting for a drift between the first pressure measurements from the pressure sensing intravascular catheter and the second pressure measurements from the pressure transducer of the pressure sensing intravascular guidewire; and output the calculated pressure ratios to a display.

6. The system of claim 5, wherein the values added to the pressure ratios increase non-linearly over time.

7. The system of claim 5, wherein the calculated pressure ratios are constrained such that the pressure ratios increase in correspondence with the pressure sensing intravascular guidewire moving from the position distal of the stenosis to the position proximal of the stenosis.

8. The system of claim 5, further comprising:
the pressure sensing intravascular catheter.

9. The system of claim 8, further comprising:
a pressure sensor,
wherein the pressure sensing intravascular catheter comprises a proximal portion, a distal portion positioned within the vessel, and a fluid column extending along a length of the pressure sensing intravascular catheter, wherein the pressure sensor is in communication with the fluid column.

10. The system of claim 9, further comprising:
a hemostasis valve fluidly coupled to the fluid column, a manifold fluidly coupled to the hemostasis valve, and tubing fluidly coupled to at least one of the hemostasis valve or the manifold, wherein the pressure sensor is in fluid communication with the fluid column via the hemostasis valve, manifold, and the tubing.

11. The system of claim 5, wherein the series of linearly increasing values added to the pressure ratios are additionally determined based at least in part on known drift characteristics of the pressure sensing intravascular guidewire.

12. The system of claim 5, wherein the series of linearly increasing values added to the pressure ratios are additionally determined based at least in part on known drift characteristics of the pressure sensing intravascular catheter.

13. The system of claim 5, wherein calculating the pressure ratios further includes constraining the pressure ratios such that each pressure ratio is equal to or larger than the pressure ratios calculated with pressure measurements of the second pressure measurements taken at positions distal to the position at which an additional pressure measurement of the second pressure measurements corresponding to the pressure ratio is taken and is equal to or smaller than the pressure ratios calculated with pressure measurements of the second pressure measurements taken at positions proximal to the position at which the additional pressure measurement of the second pressure measurements corresponding to the pressure ratio is taken.

14. The system of claim 5, wherein calculating the pressure ratios further includes alerting a user when one or more of the values added to the pressure ratios exceeds a predetermined threshold.

15. The system of claim 14, wherein the alert comprises a recommendation to retake the second pressure measurements.

16. The system of claim 5, wherein calculating the pressure ratios further includes outputting a graphic representative of the automatic correction to the display.

17. The system of claim 16, wherein calculating the pressure ratios further includes receiving an instruction from a user to accept or reject the automatic correction.

18. The system of claim 5, wherein the pressure sensing intravascular guidewire comprises a housing disposed at the distal portion of the shaft, wherein the pressure transducer is positioned within the housing, and wherein the pressure transducer is spaced from a distal end of the distal portion of the shaft.

19. The system of claim 5, wherein the pressure transducer is a piezo-electric transducer.

* * * * *